United States Patent [19]
Suzuki et al.

[11] Patent Number: 5,260,439

[45] Date of Patent: Nov. 9, 1993

[54] POLYMERIZABLE MONOMER HAVING AT LEAST ONE ISOPROPENYL PHENYL GROUP AND BEING CAPABLE OF FORMING A HIGH SURFACE HARDNESS TRANSPARENT RESIN

[75] Inventors: Toshiyuki Suzuki; Katsuyoshi Sasagawa; Masao Imai; Yoshinobu Kanemura, all of Kanagawa, Japan

[73] Assignee: Mitsui Toatsu Chemicals, Incorporated, Tokyo, Japan

[21] Appl. No.: 808,240

[22] Filed: Dec. 16, 1991

Related U.S. Application Data

[62] Division of Ser. No. 486,950, Mar. 1, 1990, Pat. No. 5,084,538.

[30] Foreign Application Priority Data

Mar. 1, 1989 [JP] Japan ............... 1-48919
May 22, 1989 [JP] Japan ............... 1-126629
Sep. 20, 1989 [JP] Japan ............... 1-241759

[51] Int. Cl.⁵ .......................... C07D 251/04
[52] U.S. Cl. ................. 544/222; 549/335; 558/239; 560/24; 560/32; 560/33
[58] Field of Search ......... 558/239, 240; 560/24, 560/32, 33; 549/335; 544/221, 222, 400

[56] References Cited

U.S. PATENT DOCUMENTS 4,714,772 12/1987 Colvin .................. 558/240

FOREIGN PATENT DOCUMENTS 63-75022 4/1988 Japan .

*Primary Examiner*—Christopher Henderson
*Attorney, Agent, or Firm*—Burns, Doane, Swecker & Mathis

[57] ABSTRACT

The present invention relates to a high surface hardness transparent resin having excellent scratch resistance, heat resistance and chemical resistance, a glazing material, a protective cover for display devices, an optical lens and a hard coat material comprising the aforesaid resin, and a novel polymerizable monomer which is useful as a raw material of the above-mentioned resin.

The monomer is represented by the formula (I)

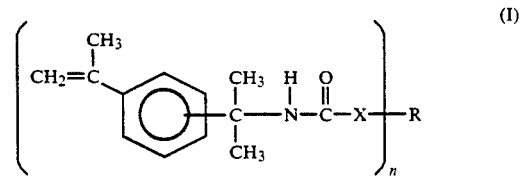

(wherein R is an aliphatic residue having or not having an halogen atom, an oxygen atom, an alicyclic ring, a heterocyclic ring or an aromatic ring, an alicyclic residue, or a heterocyclic residue, n is an integer of 1 to 4, when n=1, X is oxygen or sulfur, when n≧2, X's are all oxygen or all sulfur, one X is oxygen while the other X or X's are sulfur, one X is sulfur while the other X or X's are oxygen, or two X's are oxygen while the other X's are sulfur).

The aforesaid high surface hardness transparent resin comprises a crosslinked polymer prepared by copolymerizing a monomer (A) represented by the formula (I) and a monomer (B) having, in one molecule, m functional groups of at least one kind selected from the group consisting of $CH_2=CH-C(O)-O-$, $CH_2=C(CH_3)-C(O)-O-$ and

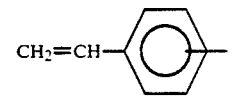

where (n+m) is an integer of 3 or more.

1 Claim, No Drawings

POLYMERIZABLE MONOMER HAVING AT LEAST ONE ISOPROPENYL PHENYL GROUP AND BEING CAPABLE OF FORMING A HIGH SURFACE HARDNESS TRANSPARENT RESIN

This application is a divisional of application Ser. No. 07/486,950, filed Mar. 1, 1990, which has now issued into U.S. Pat. No. 5,084,538.

BACKGROUND OF THE INVENTION (i) Field of the Invention

The present invention relates to a transparent resin which has high surface hardness and exhibits excellent scratch resistance, heat resistance and chemical resistance. The invention also relates to a glazing material, a protective cover for display devices, an optical lens and a hard coat material comprising the resin and a novel polymerizable monomer useful as a raw material for the high surface hardness transparent resin.

(ii) Description of the Prior Art

Methacrylic resin, polycarbonate resin and polystyrene resin exhibit excellent transparency, impact resistance, workability and mass productivity, and therefore have been used as a glazing material such as for windowpanes in vehicles, houses, schools and sports facilities, baseboards of verandas, and balconies, protective covers for display devices such as various dashboards, displays for computers, liquid crystal televisions and front boards of vending machines, optical lenses, illuminator covers, signboards, protective glasses, optical photodisc substrates and the like. Particularly, when the above-mentioned resins are applied as glazing materials, protective covers for display devices and as optical lenses, it is necessary that such resins have high scratch resistance, i.e., high surface hardness, chemical resistance, heat resistance and the like to achieve good visibility and desired appearance transparency, optical physical properties, mechanical strength stiffness and the like.

However, the above-mentioned transparent resins are linear polymers, and therefore do not exhibit the requisite surface hardness, chemical resistance and heat resistance. In addition, even if these resins are coated with a hard coat to improve their surface hardness and chemical resistance, sufficient performance cannot always be obtained.

For the purpose of solving these problems, a transparent resin has been proposed which comprises a polymer having a crosslinking structure such as diethylene glycol diallylcarbonate resin or a urethane polyacrylate (Japanese Patent Laid-open Publication Nos. 3610/1986 and 75022/1988).

However, the proposed resins are prepared by the mutual polymerization of an allyl group, an acrylic group or a methacylic group, polymerization rates of which are on a similar and therefore problems exist such as difficulty of controlling the rate of polymerization run-away reactions and a long period of time is required to obtain a polymer having a good surface state and a low polymerization strain.

SUMMARY OF THE INVENTION

The present invention overcomes the problems and disadvantages of the prior art by providing a high surface hardness transparent resin prepared by combining an isopropenylphenyl group having a low polymerization rate with another polymerizable group having a high polymerization rate, i.e. by copolymerizing a compound having at least one isopropenylphenyl groups in one molecule thereof and another compound having an acryloyl group, a methacryloyl group or a vinylphenyl group in which the radical polymerizability is higher than in the isopropenylphenyl group.

An object of the present invention is to provide a transparent resin which can be prepared by an easily controlled polymerization reaction and which has a high surface hardness and exhibits excellent chemical resistance and heat resistance.

Another object of the present invention is to provide a monomer having a polymerizable group which has a polymerization rate slower than an acrylic group, a methacrylic group and a vinylphenyl group and which exhibits excellent copolymerizability with these groups, and which can be formed into a polymer having a high surface hardness and excellent transparency, heat resistance and chemical resistance properties.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, in a first embodiment, the present invention provides a high surface hardness transparent resin comprising a crosslinked polymer prepared by copolymerizing a monomer (A) represented by the formula (I)

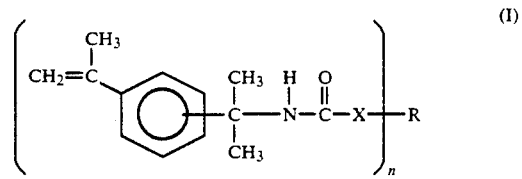

(wherein R is an aliphatic residue having or not having a halogen atom, an oxygen atom, an alicyclic ring, a heterocyclic ring or an aromatic ring, an alicyclic residue, or a heterocyclic residue, n is an integer of 1 to 4, when n=1, X is oxygen or sulfur, when n≧2, X's are all oxygen or all sulfur, one X is oxygen while the other X or X's are sulfur, one X is sulfur while the other X or X's are oxygen, or two X's are oxygen while the other X's are sulfur) and a monomer (B) having, in one molecule, m functional groups of at least one kind selected from the group consisting of $CH_2=CH-C(O)-O-$, $CH_2=C(CH_3)-C(O)-O-$ and

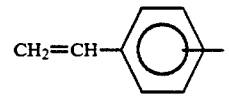

where (n+m) is an integer of 3 or more.

In a second embodiment, the present invention provides a high surface hardness transparent resin comprising a crosslinked polymer containing a structural unit represented by the following formula (II) and/or (III) comprising the monomer (A) and the monomer (B) set forth above:

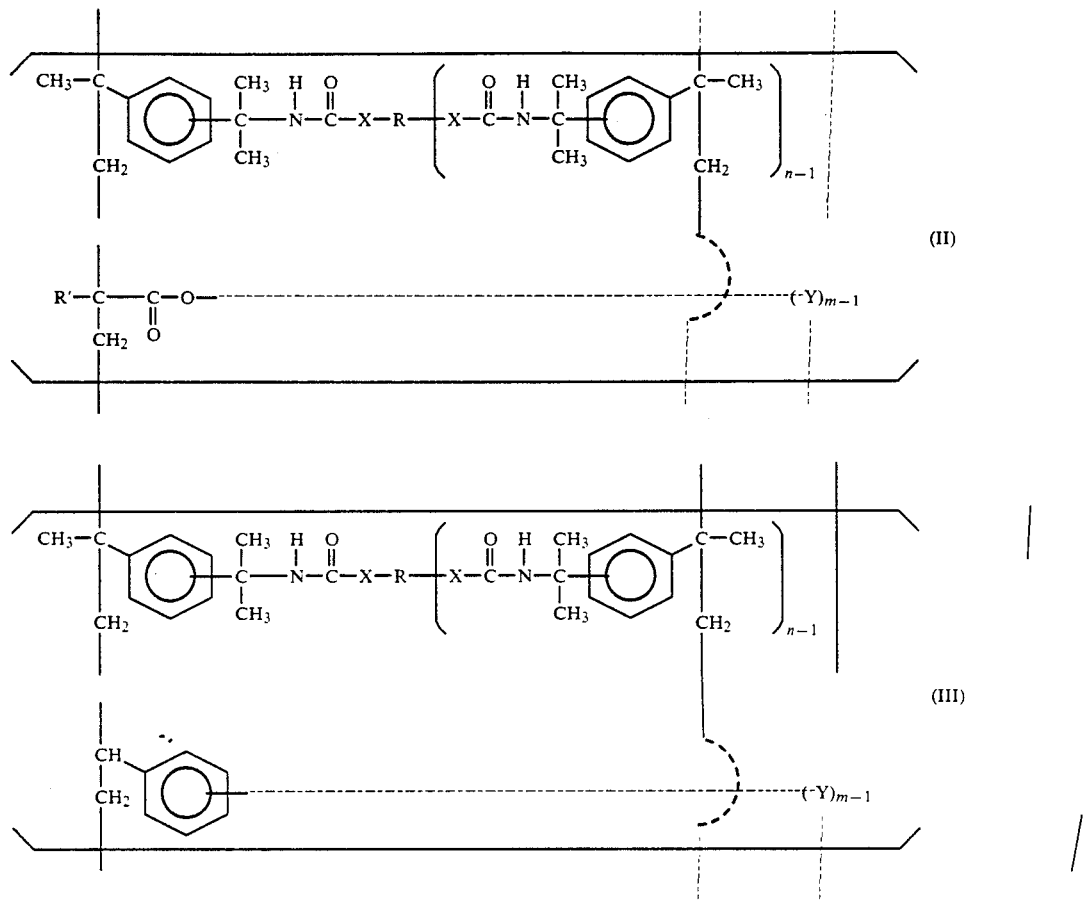

(wherein X is oxygen or sulfur, R is an aliphatic residue having or not having a halogen atom, an oxygen atom, an alicyclic ring, a heterocyclic ring or an aromatic ring, an alicyclic residue, or a heterocyclic residue, R' is hydrogen or methyl, Y is, similar or dissimilar,

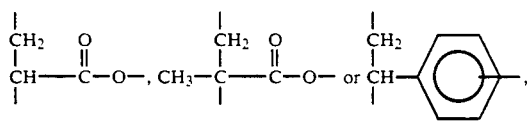

n is an integer of 1–4, and ( n+m ) is an integer of 3 or more).

In a third embodiment, the present invention provides a glazing material comprising a high surface hardness transparent resin described in the first embodiment of the invention.

In a fourth embodiment the present invention provides a protective cover for display devices comprising the high surface hardness transparent resin described in the first embodiment of the invention.

In a fifth embodiment the present invention provides an optical lens comprising the high surface hardness transparent resin described in the first embodiment of the invention.

In sixth embodiment the present invention provides a hard coat material comprising the high surface hardness transparent resin described in the first embodiment of the present invention.

In a seventh embodiment of the present invention provides a high surface hardness transparent resin comprising a crosslinked polymer prepared by copolymerizing a monomer (A) of at least one kind selected from the group consisting of monomers represented by the formulae (IV), (V) and (VI):

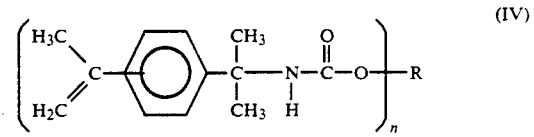

wherein when n is 1, R is selected from the group consisting of —CH$_3$, —C$_2$H$_5$, —C$_3$H$_7$, —C$_4$H$_9$, —C$_5$H$_{11}$, —C$_6$H$_{13}$, —CH$_2$CCl$_3$, —CH$_2$CF$_3$,

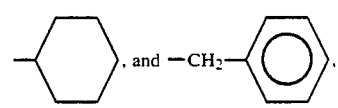

and the substituent on the aromatic ring is present at the m-position or the p-position thereof,

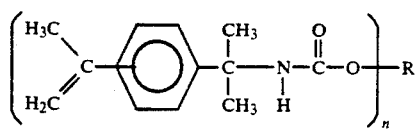 (V)

wherein when n is 2, R is selected from the group consisting of

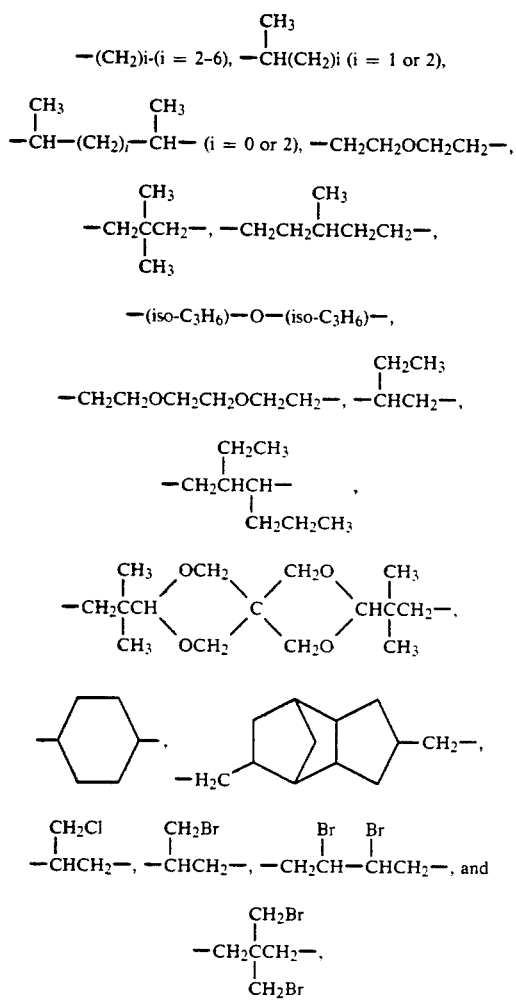

and the substituent on the aromatic ring is present at the m-position or the p-position thereof,

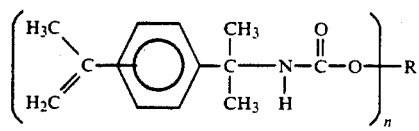 (VI)

wherein when n is 3, R is selected from the group consisting of

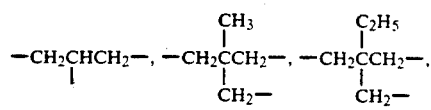

-continued

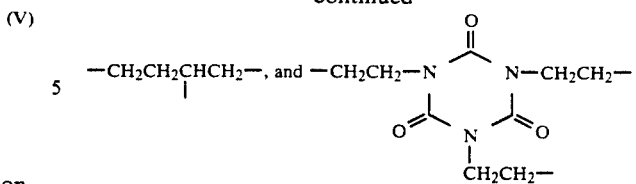

and the substituent on the aromatic ring is present at the m-position or the p-position thereof and a monomer (B) having, in one molecule, m functional groups of at least one kind selected from the group consisting of $CH_2=CH-C(O)-O-$, $CH_2=C(CH_3)-C(O)-O-$ and

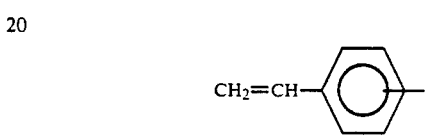

where the sum of ( n+m ) is an integer of 3 or more.

In an eighth embodiment the present invention is directed to a polymerizable monomer represented by the formula (I), especially, the formula (VII) below,

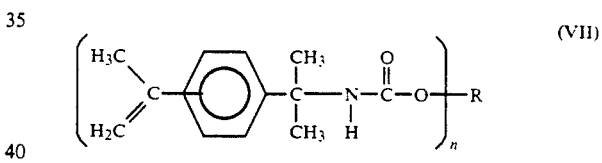 (VII)

wherein n is 2 or 3, R is selected from the group consisting of

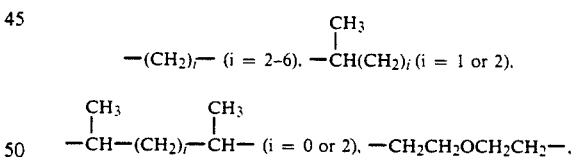

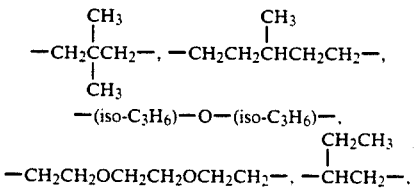

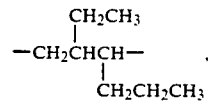

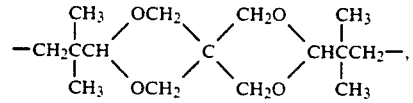

-continued

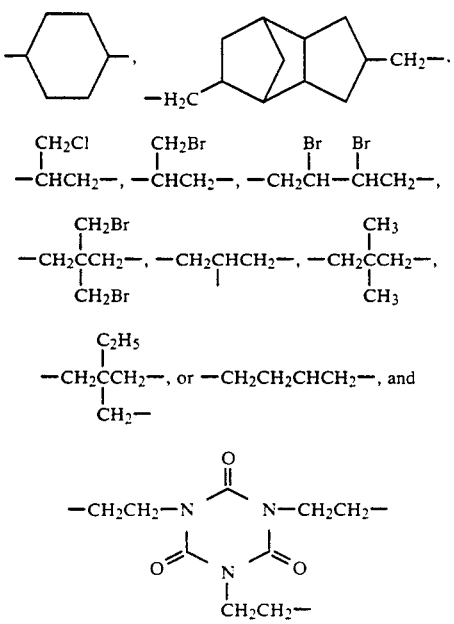

and the substituent on the aromatic ring is present at the m-position or the p-position thereof.

The inventors have found that run-away reactions can be easily controlled during polymerization; and polymerization time can be noticeably shortened.

In addition, it has also been found that the resin of the present invention has a high surface hardness, i.e., scratch resistance, heat resistance and chemical resistance, and therefore plate materials comprising this resin are useful as glazing materials such as window-panes in vehicles houses, schools and sports facilities, baseboards of verandas, and balconies, protective covers for display devices such as various dashboards, displays for computers, liquid crystal televisions and front boards of vending machines, and optical lenses. Furthermore, it has been found that the resin of the present invention is also useful as a coating film, i.e., hard coat material, because when the resin is applied onto a resin, a metal or a lumber material and then polymerized, the obtained hard coat has excellent scratch resistance and chemical resistance.

DESCRIPTION OF THE PREFERRED EMBODIMENTS

Reference will now be made in detail to the present preferred embodiments of the invention.

Exemplary suitable monomers (A) represented by the following formula (I) of the present invention

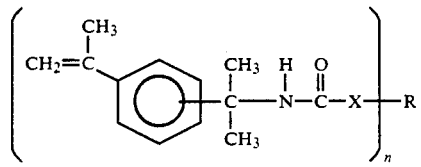

(wherein R is an aliphatic residue having or not having a halogen atom, an oxygen atom, an alicyclic ring, a heterocyclic ring or an aromatic ring, an alicyclic residue, or a heterocyclic residue, n is an integer of 1 to 4, when n=1, X is oxygen or sulfur, when n≧2, X's are all oxygen or all sulfur, one X is oxygen while the other X or X's are sulfur, one X is sulfur while the other X is X's are oxygen, or two X's are oxygen while the other X's are sulfur) include a carbamic acid ester or a thiocarbamic acid ester obtained by reacting isopropenyl-α,α-dimethylbenzyl isocyanate with a compound having from 1 to 4 OH groups and SH groups and an aliphatic residue which may or may not contain a halogen atom, an oxygen atom, an alicyclic ring, a heterocyclic ring or aromatic ring, an alicyclic residue or a heterocyclic residue, i.e., reacting the isocyanate group of isopropenyl-α,α-dimethylbenzyl isocyanate with the OH group or SH group. Here, compounds of the formula (I) where when n is 2 or more, X's are all oxygen or all sulfur, or when one or two X's are oxygen and the other X being sulfur, or one X is sulfur and the other X being oxygen, can be included.

Usually, the lower the molecular weight of the residue R, the better, depending upon the steric firmness of its structure. Preferably, the molecular weight of the residue R is from 15 to 500. Exemplary suitable compounds having from 1 to 4 OH groups or SH groups and an aliphatic residue which may or may not have a halogen atom, an oxygen atom, an alicyclic ring, a heterocyclic ring or an aromatic ring, an alicyclic residue or a heterocyclic residue which are used in preparing the monomer (A) by the above-mentioned method include methanol, ethanol, propanol, butanol, pentanol, hexanol, heptanol, octanol, cyclopentanol, cyclohexanol, cycloheptanol, cyclooctanol, 2,2,2-trichloroethanol, 2,2,2-trifluoroethanol, 1,3-dichloro-2-propanol, 2,3-dichloro-1-propanol, 2,3-dibromo-1-propanol, 1-chloro-2-propanol, 3-chloro-1-propanol, 2-chloroethanol, 2-bromoethanol, methanethiol, ethanethiol, propanethiol, butanethiol, pentanethiol, hexanethiol, heptanethiol, octanethiol, cyclohexanethiol, benzyl alcohol, ethylene glycol, 1,3-propanediol, 1,4-butanediol, 1,4-butenediol, 1,5-pentanediol, 1,6-hexanediol, 1,2-propanediol, 1,3-butanediol, 2,3-butanediol, 2,5-hexanediol, diethylene glycol, neopentyl glycol, 3-methyl-1,5-pentanediol, dipropylene glycol, triethylene glycol, 1,2-butanediol, 2-ethyl-1,3-hexanediol, spiro glycol, 1,4-cyclohexanediol, tricyclo[5,2,1,02,6]decane-4,8-dimethanol, 3-chloro-1,2-propanediol, 3-bromo-1,2 propanediol, 2,3-dibromo 1,4-butanediol, dibromoneopentyl glycol, bisphenol A (2-hydroxyethyl) ether, bisphenol F (2-hydroxyethyl) ether, bisphenol S (2-hydroxyethyl) ether, biphenol (2-hydroxyethyl) ether, tetrabromobisphenol A (2-hydroxyethyl) ether, benzenedimethanol, ethanedithiol, propanedithiol, butanedithiol, pentanedithiol, hexanedithiol, propanetrithiol, eyclohexanedithiol, ethylene glycol bis(2-mercaptoacetate), ethylene glycol bis(3-mercaptopropionate), bis(mercaptomethyl)benzene, 2-hydroxyethyl disulfide, 2-mercaptoethanol, 1-mercapto-2-propanol, glycerol, trimethylolethane, trimelthylolpropane, 1,2,4-butanetriol, 1,2,6-hexanetriol, 1,3,5-tris(2-hydroxyethyl)cyanuric acid, pentaerythritol, threitol, 3-mercapto-1,2-propanediol, pentaerythritol tetrakis(2-mercapto acetate) and pentaerythritol tetrakis(3-mercapto propionate). The carbamic acid ester or thiocarbamic acid ester can be produced from the above-mentioned compounds by the reaction between the isocyanate group of isopropenyl-α,α-dimethylbenzyl isocyanate and the OH group or the SH group. At this time, a tin compound such as dibutyltin dilaurate, dimethyltin dichloride and the like or an amine such as morpholine, dimethylaminobenzene and the like may be added thereto as a catalyst to accelerate the synthetic reaction. Preferably, a tin compound is added to prevent coloring in a subsequent radical reaction. When a solvent is used, the solvent should be distilled off after completion of the synthetic reaction. If necessary, purification may be further carried out, and the thus obtained product may be used as the monomer (A) in the subsequent radical polymerization.

Exemplary suitable monomers (A) for use in the invention include compounds represented by the formulae (IV), (V) and (VI):

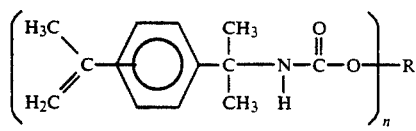
(IV)

wherein when n is 1, R is selected from the group consisting of —CH$_3$, —C$_2$H$_5$, —C$_3$H$_7$, —C$_4$H$_9$, —C$_5$H$_{11}$, —C$_6$H$_{13}$, —CH$_2$CCl$_3$, —CH$_2$CF$_3$,

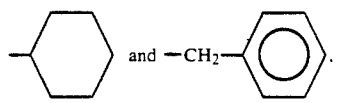

and the substituent on the aromatic ring is present at the m-position or the p-position thereof.

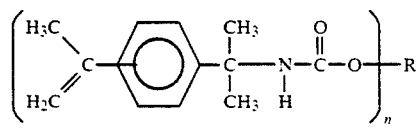
(V)

wherein when n is 2, R is selected from the group consisting of —(CH$_2$)$_i$— wherein i=2-6,

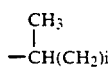

wherein i=1 or 2,

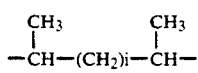

wherein i=0 or 2, —CH$_2$CH$_2$OCH$_2$CH$_2$—,

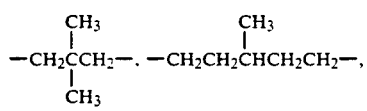

—(iso-C$_3$H$_6$)—O—(iso-C$_3$H$_6$)—,

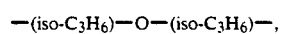

—CH$_2$CH$_2$OCH$_2$CH$_2$OCH$_2$CH$_2$—, 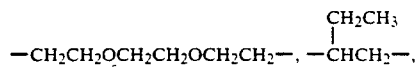

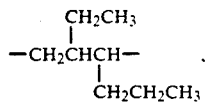

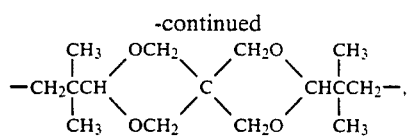

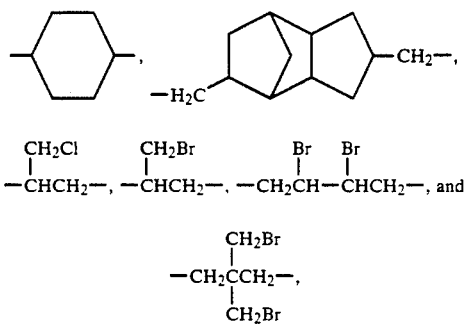

and the substituent on the aromatic ring is present at the m-position or the p-position thereof.

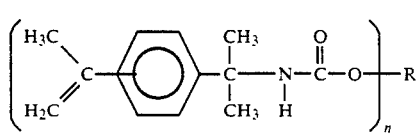
(VI)

wherein when n is 3, R is selected from the group consisting of

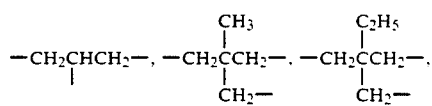

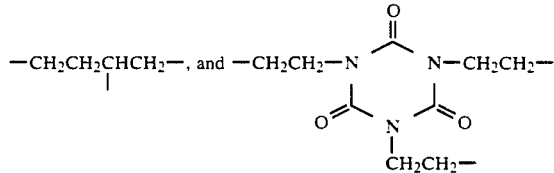

and the substituent on the aromatic ring is present at the m-position or the p-position thereof. Further examples of the monomer (A) are:

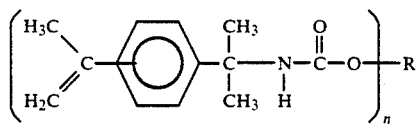

(wherein n=4, R is

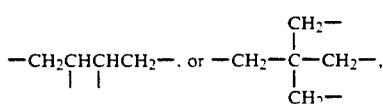

the substituents on the aromatic ring are at m- or p-position),

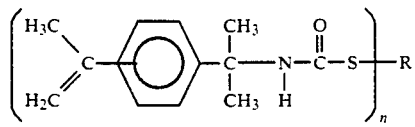

(wherein when n=2, R is —(CH₂)ᵢ—(i=2-6),

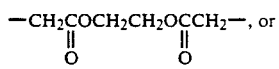

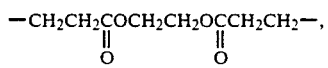

the substituents on the aromatic ring are at m- or p-position), and

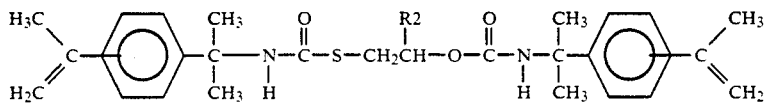

(wherein R2 is H or —CH₃, the substituents on the aromatic ring are at m- or p-position).

The monomer B having m functional groups of one kind selected from the group consisting of

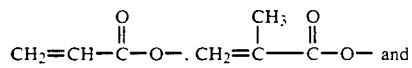

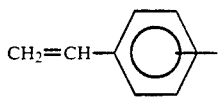

in the present invention is an ester of acrylic acid or methacrylic acid or a derivative of styrene. Exemplary suitable monomers (B) in which m is 1 for use in the invention include methyl acrylate, methyl methacrylate, ethyl acrylate, ethyl methacrylate, propyl acrylate, propyl methacrylate, isopropyl acrylate, isopropyl methacrylate, cyclohexyl acrylate, cyclohexyl methacrylate, benzyl acrylate, benzyl methacrylate, methoxyethyl acrylate, methoxyethyl methacrylate, ethoxyethyl acrylate, ethoxyethyl methacrylate, 2-hydroxyethyl acrylate, 2-hydroxyethyl methacrylate, 2-hydroxypropyl acrylate, 2-hydroxypropyl methacrylate, 1,4-butylene glycol monoacrylate, 1,4-butylene glycol monomethacrylate, glycidyl acrylate, glycidyl methacrylate, styrene, methylstyrene, chlorostyrene, bromostyrene, chloromethylstyrene and methoxystyrene.

Exemplary suitable monomers (B) in which m is 2 or more include ethylene glycol diacrylate, ethylene glycol dimethacrylate, diethylene glycol diacrylate, diethylene glycol dimethacrylate, propylene glycol diacrylate, propylene glycol dimethacrylate, dipropylene glycol diacrylate, dipropylene glycol dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, 2,2-bis(4-acryloxypropyloxyphenyl)propane, 2,2-bis(4-methacryloxypropyloxyphenyl)propane, 1,3-butanediol diacrylate, 1,3-butanediol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, neopentyl glycol hydroxypivalate diacrylate, spiroglycol diacrylate, spiroglycol dimethacrylate, epoxy acrylate, epoxy methacrylate, 2-propenoic acid [2-[1,1-dimethyl-2-[(1-oxo-2-propenyl)oxy]ethyl]-5-ethyl-1,3-dioxane-5-yl]methyl ester, trimethylolpropane triacrylate, trimethylolpropane trimethacrylate, pentaerythritol triacrylate, pentaerythritol trimethacrylate, bis(acryloyloxyethyl)hydroxyethyl isocyanurate, bis(methacryloyloxyethyl)hydroxyethyl isocyanurate, tris(acryloyloxyethyl) isocyanurate, tris(methacryloyloxyethyl) isocyanurate, pentaerythritol tetraacrylate, pentaerythritol tetramethacrylate, dipentaerythritol hexaacrylate, dipentaerythritol hexamethacrylate, methyltri(acryloyloxyethoxy)silane, glycerol diacrylate, glycerol dimethacrylate, glycerol methacrylate acrylate, dibromoneopentyl glycol diacrylate, dibromoneopentyl glycol dimethacrylate, divinylbenzene, urethane acrylates, urethane methacrylates, 1,1,3,3,5,5-hexa(acryloyloxy)cyclotriphosphazene, 1,1,3,3,5,5-hexa(methacryloyloxy)cyclotriphosphazene, 1,1,3,3,5,5-hexa(acryloylethylenedioxy)cyclotriphasphozene and 1,1,3,3,5,5-hexa(methacryloylethylenedioxy)cyclotriphosphazene.

In the present invention, the transparent resin having a high surface hardness can be prepared by copolymerizing a monomer (A) represented by the formula (I)

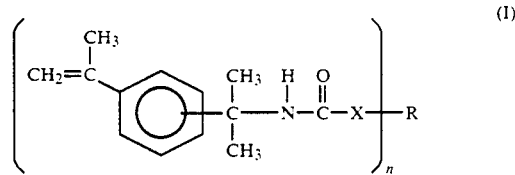

(wherein R is an aliphatic residue having or not having a halogen atom, an oxygen atom, an alicyclic ring, a heterocyclic ring or an aromatic ring, an alicyclic residue, or a heterocyclic residue, n is an integer of 1 to 4, when n=1, X is oxygen or sulfur, when n≧2, X's are all oxygen or all sulfur, one X is oxygen while the other X or X's are sulfur, one X is sulfur while the other X or X's are oxygen, or two (B) having, in one molecule, m functional groups of at least one kind selected from the group consisting of CH₂=CH—C(O)—O—, CH₂=C(CH₃)—C(O)—O—and

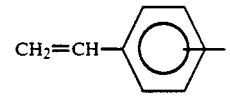

in such a ratio that (n+m) is an integer of 3 or more.

For the purpose of adjusting viscosity and the like, a monomer having an isopropenylphenyl group other than the above-mentioned monomer (A) may be additionally used.

Exemplary suitable additional monomers include diisoropenylbenzene, N-(3-isopropenyl-α,α-dimethylbenzyl)-2-acryloyloxy carbamate and N-(3-isopropenyl-α,α-dimethltenzyl)-2-methacryloyloxy carbamate.

In this copolymerization, the ratio of the isopropenyl group to

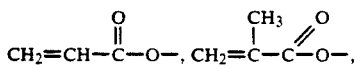

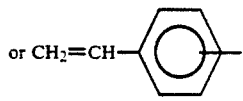

in the above-mentioned monomers depends on the type of functional groups in the monomers and the structures of the monomers, Preferably the copolymerization is carried out in a ratio of the isopropenylphenyl group: the total of

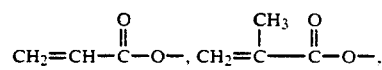

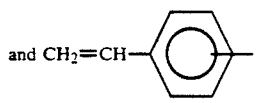

of 1 equivalent: 0.5–10 equivalents.

The copolymerization in the present invention is a radical copolymerization and can be accomplished by heat polymerization or by a means using ultraviolet rays, γrays, or the like or a combination thereof.

When the heat polymerization is carried out, the radical polymerization initiator is not limited to any particular one, but a known radical polymerization initiator can optionally be used, Exemplary suitable initiators include peroxides such as benzoyl peroxide, p-chlorobenzoyl peroxide, diisopropyl peroxy carbonate, di-2-ethylhexyl peroxy carbonate and carbonate and t-butylperoxy pivalate and an azo compound such as azobisisobutyronitrile. This initiator preferably used in an amount of from 0.01 to 5 % by weight.

When the ultraviolet rays are utilized, the optical sensitizer is not particularly limited, but a known optical sensitizer can optionally be used.

Exemplary suitable sensitizers include benzoyl compounds, tenzoin methyl ether, benzoin ethyl ether, benzoin propyl ether, benzoin isobutyl ether, 2-hydroxy-2-benzoylpropane, azobisisobutyronitrile, benzil, thioxanthone and diphenyl disulfide. This sensitizer is preferably used in an amount of from 0.01 to 5 % by weight. When a radiation such as γray and the like is utilized, the polymerization initiator and the like are not always necessary.

In the present invention, the process for preparing plates or lenses of the high surface hardness, transparent resin is not particularly limited. Known processes can be used. A typical process is a casting polymerization process. For example, a mixture of the above-mentioned monomers is mixed with a radical polymerization initiator or an optical sensitizer sufficiently, followed by defoaming. Afterward, the mixture is poured into a glass or metallic mold with which a gasket or a spacer is combined, and is then cured by heating or the irradiation by ultraviolet rays or radiation. Additives may be added to the mixture prior to polymerization. Exemplary suitable additives include ultraviolet absorbents, oxidation inhibitors, dyes, infrared absorbents, release agents and antistatic agents.

These additives should be used in amounts such that they do not prevent polymerization and curing.

When the high surface hardness transparent resin is used for the preparation of coating films, a known coating film manufacturing process may be employed. For example, a radical polymerization initiator or an optical sensitizer is added to a mixture of the above-mentioned monomers, and if necessary, the mixture is diluted with a solvent. Afterward, a substrate made of a resin, a metal, a lumber material or the like is coated with the mixture by roll coating, spray coating, flow coating, dipping or the like. When the solvent is used, it is volatilized, and curing is then carried out by heating or by the irradiation by ultraviolet rays or radiation. In this case, additives, a filler and the like can be added to the mixture prior to the polymerization. Exemplary suitable additives include an ultraviolet absorbents, oxidation inhibitors, dyes, pigments, infrared absorbents, antistatic agents and fine inorganic compound grains. These additives should be used in amount such that they do not prevent the polymerization and curing.

The thus obtained high surface hardness transparent resin plate can be used as a glazing material and a protective cover for display devices and has high scratch resistance, chemical resistance, heat resistance and excellent workability. In addition, when polymerization is carried out in a mold for lenses, or when the resin is processed by cutting and polishing. optical lenses having the same characteristics as in the above case can be obtained.

Morever, the high-hardness transparent resin can be used as a coating material, i.e., a hard coat material that exhibits excellent scratch resistance, chemical resistance and the like on another resin, a metal, a lumber material or the like.

The novel polymerizable monomer of the present invention is the above-mentioned monomer (A). Exemplary suitable polymerizable monomers include 1,2-bis[N-(3-isopropenyl-α,α-dimethylbenzyl)carbamoyloxy]ethane, 1,2-bis[N-(4-isopropenyl-α,α-dimethylbenzyl)carbamoyloxy]ethane, 1-[N-(3-isopropenyl-α,α-dimethylbenzyl)carbamoyloxy]-2-[N-(4-isopropenyl-α,α-dimethylbenzyl)carbamoyloxy]ethane, 1,3-bis[N-(3-isopropenyl-α,α-dimethylbenzyl)carbamoyloxy]propane, 1,3,-bis[N-(4-isopropenyl-α,α-dimethylbenzyl)carbamoyloxy]propane, 1-[N-(3-isopropenyl-α,α-dimethylbenzyl)-carbamoyloxy]-3-[N-4-isopropenyl-α,α-dimethylbenzyl)carbamoyloxy]propane, 1,4-bis[N-(3-isopropenyl-α,α-dimethylbenzyl)carbamoyloxy]butane, 1,4-bis[N-(4-isopropenyl-α,α-dimethylbenzyl)carbamoyloxy]butane, 1-[N-(3-isopropenyl-α,α-dimethylbenzyl)carbamoyloxy]-4-[N-(4-isopropenyl-α,α-dimethylbenzyl)carbamoyloxy]butane, 1,5-bis[N-(3-isopropenyl-α,α-dimethylbenzyl)carbamoyloxy]pentane, 1,5-bis[N-(4-isopropenyl-α,α-dimethylbenzyl)carbamoyloxy]pentane, 1-[N-(3-isopropenyl-α,α-dimethylbenzyl)carbamoyloxy]-5-[N-(4-isopropenyl-α,α-dimethylbenzyl)carbamoyloxy]pentane, 1,6-bis[N-(3-isopropenyl-α,α-dimethylbenzyl)carbamoyloxy]hexane, 1,6-bis[N-(4-isopropenyl-α,α-dimethylbenzyl)carbamoyloxy]hexane, 1-[N-(3-isopropenyl-α,α-dimethylbenzyl)carbamoyloxy]-6-[N-(4-isopropenyl-α,α-dimethylbenzyl)carbamoyloxy]hexane, 1,2-bis[N-(3-isopropenyl-α,α-dimethylbenzyl)carbamoyloxy]-propane, 1,2-bis[N-(4-isopropenyl-α,α- dimethylbenzyl)carbamoyloxy]propane, 1-[N-(3-isopropenyl-α,α-dimethylbenzyl)carbamoyloxy]-2-[N-(4-isopropenyl-α,α-dimethylbenzyl)carbamoyloxy]propane, 1,3-bis[N-(3-isopropenyl-α,α-dimethylbenzyl)carbamoyloxy]butane, 1,3-bis[N-(4-isopropenyl-α,α-dimethylbenzyl)carbamoyloxy]butane, 1-[N-(3-isopropenyl-α,α-dimethylbenzyl)carbamoyloxy]-3-(N-(4-isopropenyl-α,α-dimethylbenzyl)carbamoyloxy]butane, 2,3-bis[N-(3-isopropenyl-α,α-dimethylbenzyl)carbamoyloxy]butane, 2,3-bis[N-(4-isopropenyl-α,α-dimethylbenzyl)carbamoyloxy]butane, 2-[N-(3-isopropenyl-α,α-dimethylbenzyl)carbamoyloxy]-3-[N-(4-isopropenyl-α,α-dimethylbenzyl)carbamoyloxy]butane, 2,5-bis[N-(3-isopropenyl-α,α-dimethylbenzyl)carbamoyloxy]hexane, 2,5-bis[N-(4-isopropenyl-α,α-dimethylbenzyl)carbamoyloxy]-hexane, 2-[N-(3-isopropenyl-α,α-dimethylbenzyl)carbamoyloxy]-5-[N-(4-isopropenyl-α,α-dimethylbenzyl)carbamoyloxy]hexane, bis[2-(N-(3-isopropenyl-α,α-dimethylbenzyl)carbamoyloxy)ethyl]ether, bis[2-(N-(4-isopropenyl-α,α-dimethylbenzyl)carbamoyloxy)ethyl]ether, [2-(N-(3-isopropenyl-α,α-dimethylbenzyl)carbamoyloxy)ethyl]-[2'-(N-(4-isopropenyl-α,α-dimethylbenzyl)carbamoyloxy)ethyl]ether, 2,2-dimethyl-1,3-bis[N-(3-isopropenyl-α,α-dimethylbenzyl)carbamoyloxy]-propane, 2,2-dimethyl-1,3-bis[N-(4-isopropenyl-α,α-dimethylbenzyl)carbamoyloxy]propane, 2,2-dimethyl-1-[N-(3-isopropenyl-α,α-dimethylbenzyl)carbamoyloxy]-3-[N-(4-isopropenyl-α,α-dimethylbenzyl)carbamoyloxy]propane, 3-methyl-1,5-bis[N-(3-isopropenyl-α,α-dimethylbenzyl)carbamoyloxy]pentane, 3-methyl-1,5-bis[N-(4-isopropenyl-α,α-dimethylbenzyl)carbamoyloxy]pentane, 3-methyl-1-[N-(3-isopropenyl-α,α-dimethylbenzyl)carbamoyloxy]-5-[N-(4-isopropenyl-α,α-dimethylbenzyl)carbamoyloxy]pentane, bis[N-(3-isopropenyl-α,α-dimethylbenzyl)carbamoyloxy)isopropyl]ether, bis[(N-(4-isopropenyl-α,α-dimethylbenzyl)carbamoyloxy)isopropyl]ether, [(N-(3-isopropenyl-α,α-dimethylbenzyl)carbamoyloxy)isopropyl][(N-(4-isopropenyl-α,α-dimethylbenzyl)carbamoyloxy) isopropyl] ether, bis[2-(N-(3-isopropenyl-α,α-dimethylbenzyl)carbamoyloxy)ethoxy]ethane, bis[2-(N-(4-isopropenyl-α,α-dimethylbenzyl)carbamoyloxy)ethoxy]ethane, [2-(N-(3-isopropenyl-α,α-dimethylbenzyl)carbamoyloxy)ethoxy]-[2'-(N-(4-isopropenyl-α,α-dimethylbenzyl)carbamoyloxy)ethoxy]ethane, 1,2-bis[N-(3-isopropenyl-α,α-dimethylbenzyl)carbamoyloxy]butane, 1,2-bis[N-(4-isopropenyl-α,α-dimethylbenzyl)carbamoyloxy]butane, 1-[N-(3-isopropenyl-α,α-dimethylbenzyl)carbamoyloxy]-2-[N-(4-isopropenyl-α,α-dimethylbenzyl) carbamoyloxy]butane, 1-[N-(4-isopropenyl-α,α-dimethylbenzyl)carbamoyloxy]-2-[N-(3-isopropenyl-α,α-dimethylbenzyl) carbamoyloxy]butane, 2-ethyl-1,3-bis[N-(3-isopropenyl-α,α-dimethylbenzyl)carbamoyloxy]hexane, 2-ethyl-1,3-bis[N-(4-isopropenyl-α,α-dimethylbenzyl)carbamoyloxy]hexane, 2-ethyl-1-[N-(3-isopropenyl-α,α-dimethylbenzyl)carbamoyloxy]-3-[N-(4-isopropenyl-α,α-dimethylbenzyl)carbamoyloxy]hexane, 2-ethyl-1-[N-(4-isopropenyl-α,α-dimethylbenzyl)carbamoyloxy]-3-[N-(3-isopropenyl-α,α-dimethylbenzyl)carbamoyloxy]hexane, 3,9-bis[1,1-dimethyl-2-(N-(3-isopropenyl-α,α-dimethylbenzyl)carbamoyloxy)ethyl]-2,4,8,10-tetraoxaspiro (5,5)undecane, 3,9-bis[1,1-dimethyl-2-(N-(4-isopropenyl-α,α-dimethylbenzyl)carbamoyloxy)ethyl]-2,4,8,10-tetraoxaspiro (5,5)undecane, 3-[1,1-dimethyl-2-(N-(3-isopropenyl-α,α-dimethylbenzyl)carbamoyloxy)ethyl]-9-[1,1-dimethyl-2-(N-(4-isopropenyl-α,α-dimethylbenzyl)carbamoyloxy)ethyl]-2,4,8,10-tetraoxaspiro(5,5)-undecane, 1,4-bis[N-(3-isopropenyl-α,α-dimethylbenzyl)carbamoyloxy]cyclohexane, 1,4-bis[N-(4-isopropenyl-α,α-dimethylbenzyl)carbamoyloxy]cyclohexane, 1-[N-(3-isopropenyl-α,α-dimethylbenzyl)carbamoyloxy]-4-[N-(4-isopropenyl-α,α-dimethylbenzyl) carbamoyloxy]cyclohexane, 4,8-bis[N-(3-isopropenyl-α,α-dimethylbenzyl)carbamoyloxymethyl]tricyclo[5,2,1,0$^{2,6}$]decane, 4,8-bis[N-(4-isopropenyl-α,α-dimethylbenzyl)carbamoyloxymethyl]tricyclo[5,2,1,0$^{2,6}$]decane, 4-[N-(3-isopropenyl-α,α-dimethylbenzyl)carbamoyloxymethyl]-8-[N-(4-isopropenyl-α,α-dimethylbenzyl) carbamoyloxymethyl]tricyclo[5,2,1,0$^{2,6}$]decane, 3-chloro-1,2 bis[N-(3-isopropenyl-α,α-dimethylbenzyl)carbamoyloxy]propane, 3-chloro-1,2-bis[N-(4-isopropenyl-α,α-dimethylbenzyl)carbamoyloxy]propane, 3-chloro-1-[N-(3-isopropenyl-α,α-dimethylbenzyl)carbamoyloxy]-2-[N-(4-isopropenyl-α,α-dimethylbenzyl)carbamoyloxy]propane, 3-chloro-1-[N-(4-isopropenyl-α,α-dimethylbenzyl)carbamoyloxy]-2-[N-(3-isopropenyl-α,α-dimethylbenzyl)carbamoyloxy]propane, 3-bromo-1,2-bis[N-(3-isopropenyl-α,α-dimethylbenzyl)carbamoyloxy]propane, 3-bromo-1,2-bis[N-(4-isopropenyl-α,α-dimethylbenzyl)carbamoyloxy]propane, 3-bromo-1-[N-(3-isopropenyl-α,α-dimethylbenzyl)carbamoyloxy]-2-[N-(4-isopropenyl-α,α-dimethylbenzyl)-carbamoyloxy]propane, 3-bromo-1-[N-(4-isopropenyl-α,α-dimethylbenzyl)carbamoyloxy]-2-[N-(3-isopropenyl-α,α-dimethylbenzyl)carbamoyloxy]propane, 2,3-dibromo-1,4-bis[N-(3-isopropenyl-α,α-dimethylbenzyl)carbamoyloxy]butane, 2,3-dibromo-1,4-bis[N-(4-isopropenyl-α,α-dimethylbenzyl)carbamoyloxy]butane, 2,3-dibromo-1-[N-(3-isopropenyl-α,α-dimethylbenzyl)carbamoyloxy]-4-[N-(4-isopropenyl-α,α-dimethylbenzyl)carbamoyloxy]butane, 2,2-dibromomethyl-1,3-bis[N-(3-isopropenyl-α,α-dimethylbenzyl)carbamoyloxy]propane, 2,2-dibromomethyl-1,3-bis[N-(4-isopropenyl-α,α-dimethylbenzyl)carbamoyloxy]propane, 2,2-dibromomethyl-1-[N-(3-isopropenyl-α,α-dimethylbenzyl)carbamoyloxy]-3-[N-(4-isopropenyl-α,α-dimethylbenzyl)carbamoyloxy]propane, 1,2,3-tris[N-(3-isopropenyl-α,α-dimethylbenzyl)carbamoyloxy]propane, 1,2-bis[N-(3-isopropenyl-α,α-dimethylbenzyl)carbamoyloxy]-3-[N-(4-isopropenyl-α,α-dimethylbenzyl) carbamoyloxy]propane, 1,3-bis[N-(3-isopropenyl-α,α-dimethylbenzyl)carbamoyloxy]-2-[N-(4-isopropenyl-α,α-dimethylbenzyl) carbamoyloxy]propane, 1,2-bis[N-(4-isopropenyl-α,α-dimethylbenzyl)carbamoyloxy]-3-[N-(3-isopropenyl-α,α-dimethylbenzyl) carbamoyloxy]propane, 1,3-bis[N-(4-isopropenyl-α,α-dimethylbenzyl)carbamoyloxy]-2-[N-(3-isopropenyl-α,α-dimethylbenzyl) carbamoyloxy]propane, 1,2,3-tris[N-(4-isopropenyl-α,α-dimethylbenzyl)carbamoyloxy]propane, 1,1,1-tris[N-(3-isopropenyl-α,α-dimethylbenzyl)carbamoyloxymethyl]ethane, 1,1-bis[N-(3-isopropenyl-α,α-dimethylbenzyl)carbamoyloxymethyl]-1-[N-(4-isopropenyl-α,α-dimethylbenzyl)carbamoyloxymethyl]ethane, 1,1-bis[N-(4-isopropenyl-α,α-dimethylbenzyl)carbamoyloxymethyl]-1-[N-(3-isopropenyl-α,α-dimethylbenzyl)carbamoyloxymethyl]ethane, 1,1,1-tris[N-(4-ispropenyl-α,α-dimethylbenzyl)carbamoyloxymethyl]ethane, 2-ethyl-2-[N-(3-isopropenyl-α,α-dimethylbenzyl)carbamoyloxymethyl]-1,3-[N-(3-isopropenyl-α,α-dimethylbenzyl)carbamoyloxy]propane, 2-ethyl-2-[N-(4-isopropenyl-α,α-dimethylbenzyl)carbamoyloxymethyl]-1,3-[N-(3-isopropenyl-α,α-dimethylbenzyl)carbamoyloxy]propane, 2-ethyl-2-[N-(3-isopropenyl-α,α-dimethylbenzyl)carbamoyloxymethyl]-1,3-[N-(4-isopropenyl-α,α-dimethylbenzyl)carbamoyloxy]propane, 2-ethyl-2-[N-(4-isopropenyl-α,α-dimethylbenzyl)carbamoyloxymethyl]-1,3-[N-(4-isopropenyl-α,α-dimethylbenzyl)carbamoyloxy]propane, 1,2,4-tris[N-(3-isopropenyl-α,α-dimethylbenzyl)carbamoyloxy]butane, 1,2-bis[N-(3-isopropenyl-α,α-dimethylbenzyl)carbamoyloxy]-4-[N-(4-isopropenyl-α,α-dimethylbenzyl) carbamoyloxy]butane, 1,4-bis[N-(3-isopropenyl-α,α-dimethylbenzyl)carbamoyloxy]-2-[N-(4-isopropenyl-α,α-dimethylbenzyl) carbamoyloxy]butane, 1,2-bis[N-(4-isopropenyl-α,α-dimethylbenzyl)carbamoyloxy]-4-[N-(3-isopropenyl-α,α-dimethylbenzyl) carbamoyloxy]butane, 1,4-bis[N-(4-isopropenyl-α,α-dimethylbenzyl)carbamoyloxy]-2-[N-(3-isopropenyl-α,α-dimethylbenzyl) carbamoyloxy]butane, 1,2,4-tris[N-(4-isopropenyl-α,α-dimethylbenzyl)carbamoyloxy]-butane, 1,3,5-tris[2-(N-(3-isopropenyl-α,α-dimethylbenzyl)carbamoyloxyethyl)]isocyanurate, 1,3-bis[2-(N-(3-isopropenyl-α,α-dimethylbenzyl)-carbamoyloxyethyl)]-5-[2-(N-(4-isopropenyl -α,α-dimethylbenzyl)carbamoyloxyethyl)]isocyanurate, 1,3-bis[2-(N-(4-isopropenyl-α,α-dimethylbenzyl)carbamoyloxyethyl)]-5-[2-(N-(3-isopropenyl -α,α-dimethylbenzyl)carbamoyloxyethyl)]isocyanurate and 1,3,5-tris[2-(N-(4-isopropenyl-α,α-dimethylbenzyl)carbamoyloxyethyl)-]isocyanurate.

The above-mentioned polymerizable monomer of the present invention can be prepared by the following procedure: A diol or a triol is allowed to react with 3-isopropenyl-α,α-dimethylbenzyl isocyanate, 4-isopropenyl-α,α-dimethylbenzyl isocyanate or a mixture thereof in the absence or in the presence of a solvent and in the absence or in the presence of a catalyst at a suitable temperature.

Exemplary suitable diols include ethylene glycol, 1,3-propanediol, 1,4-butanediol, 1,5-pentanediol, 1,6-hexanediol, 1,2-propanediol, 1,3-butanediol, 2,3-butanediol, 2,5-hexanediol, diethylene glycol, neopentyl glycol, 3-methyl-1,5-pentanediol, dipropylene glycol, triethylene glycol, 1,2-butanediol, 2-ethyl-1,3-hexanediol, 3,9-bis(1,1-dimethyl-2-hydroxyethyl)-2,4,8,10-tetraoxaspiro(5,5)undecane, 1,4-cyclohexanediol, tricyclo[5,2,1,0$^{2,6}$]decane-4,8-dimethanol, 3-chloro-1,2-propanediol, 3-bromo-1,2-propanediol, 2,3-dibromo-1,4-butanediol and dibromoneopentyl glycol. Exemplary suitable triols include triglycerol, trimethylolethane, trimethylolpropane, 1,2,4-butanetriol and 1,3,5-tris(2-hydroxyethyl)cyanuric acid. In this reaction, the amount of the 3-isopropenyl-α,α-dimethylbenzyl isocyanate, 4-isopropenyl-α,α-dimethylbenzyl isocyanate or a mixture thereof is preferably from 0.8 to 1.1 equivalents, more preferably 0.95 to 1.05 equivalents per equivalent of the hydroxyl group in the diol or the triol. Furthermore, examples of the suitable solvent include hexane, chloroform, benzene, toluene and xylene which are not reactive with the raw materials. The above-mentioned suitable catalyst is a catalyst to accelerate a urethane formation reaction such as dibutyltin dilaurate and the like. The catalyst is preferably employed in an amount of from 0.01 to 5% by weight, preferably from 0.1 to 3% by weight based on the weight of the isocyanate. The suitable reaction temperature is preferably from about 30° to 200° C., more preferably from 50° to 150° C. After completion of the reaction, the resulting reaction solution is then purified by column chromatography or another means, thereby obtaining the desired polymerizable monomer of the present invention.

The resin of the present invention has a high surface hardness and is excellent in transparency, chemical resistance and heat resistance. In addition, it is also excellent in workability such as cutting owing to the high surface hardness.

Moreover, in the preparation of the resin of the present invention, polymerization control in the polymerization step is very easy, and therefore any peeling, whiting and cracking do not occur in the molding polymerization. The resin of the present invention exhibits very good moldability and therefore accurate molding is possible.

Thus, the resin of the present invention can be suitably used as a glazing material, a protective cover for display devices, an optical lens and a hard coat material.

Furthermore, when the novel polymerizable monomer of the present invention is copolymerized with a monomer having a polymerizable group in which the polymerization rate is high, for example, an acrylic group, a methacrylic group or a vinylphenyl group, a transparent resin can be obtained which has a high surface hardness and which is excellent in heat resistance and workability such as cutting. Additionally, in the polymerization step, polymerization control is very easy. Therefore, the monomer of the present invention is useful as the raw material of the above-mentioned high-hardness transparent resin.

The present invention will be further clarified by the following examples, which are intended to be purely exemplary of the invention.

EXAMPLES

In the following examples, part and parts are by weight, unless otherwise specified.

EXAMPLE 1

6.2 parts of ethylene glycol, 30 parts of toluene, 40.3 parts of 3-isopropenyl-α,α-dimethylbenzyl isocyanate and 0.2 part of dibutyltin dilaurate were mixed. The solution was then stirred for 1 hour, while the temperature of the solution was maintained at 80° C., to carry out the reaction. After completion of the reaction, the reaction solution was concentrated. The resulting concentrate was then purified by chromatography, thereby obtaining 40.0 parts of 1,2-bis[N-(3-isopropenyl-α,α-dimethylbenzyl)carbamoyloxy]ethane in the form of colorless transparent liquid.

| Values of elemental analysis (as $C_{28}H_{36}N_2O_4$) | | | |
|---|---|---|---|
| | C | H | N |
| Found (%) | 72.13 | 7.59 | 6.21 |
| Calcd. (%) | 72.39 | 7.81 | 6.03 |

NMR(δ/CDCl$_3$)

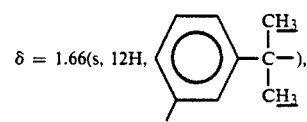

δ = 1.66(s, 12H,

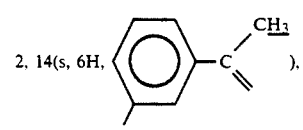

2, 14(s, 6H,

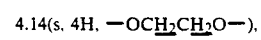

4.14(s, 4H, —OCH$_2$CH$_2$O—), 5.07(s, 2H, [structure])

5.18(s, 2H, —N(H)—), 5.34(s, 2H, [structure])

7.29(s, 6H, [structure])

7.48(s, 2H, 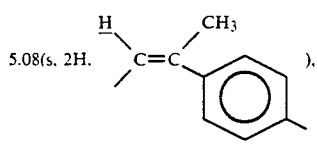)

EXAMPLE 2

6.2 parts of ethylene glycol, 30 parts of toluene, 40.3 parts of 4-isopropenyl-α,α-dimethylbenzyl isocyanate and 0.2 part of dibutyltin dilaurate were mixed. The mixed solution was then stirred for 1 hour, while the temperature of the solution was maintained at 80° C., to carry out the reaction. After completion of the reaction, the reaction solution was concentrated. The concentrated solution was then purified by chromatography, thereby obtaining 41.2 parts of 1,2-bis[N-(4-isopropenyl-α,α-dimethylbenzyl)carbamoyloxy]ethane in the form of a colorless transparent liquid.

| Values of elemental analysis (as $C_{28}H_{36}N_2O_4$) | | | |
|---|---|---|---|
| | C | H | N |
| Found (%) | 72.59 | 7.92 | 6.18 |
| Calcd. (%) | 72.39 | 7.81 | 6.03 |

NMR(δ/CDCl₃)

δ = 1.66(s, 12H, 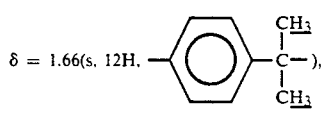), 2.14(s, 6H, 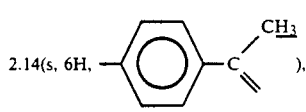), 4.14(s, 4H, —OCH₂CH₂O—), 5.08(s, 2H, [structure])

5.19(s, 2H, —N(H)—).

5.39(s, 2H, [structure])

7.35(s, 8H, [structure])

EXAMPLE 3

The same procedure as in Example 1 was repeated except that 6.2 parts of ethylene glycol was replaced with 7.6 parts of 1,3-propanediol, thereby obtaining 42.5 parts of 1,3-bis[N-(3-isopropenyl-α,α-dimethylbenzyl)-carbamoyloxy]propane in the form of a colorless transparent liquid.

| Values of elemental analysis (as $C_{29}H_{38}N_2O_4$) | | | |
|---|---|---|---|
| | C | H | N |
| Found (%) | 72.71 | 7.81 | 5.69 |
| Calcd. (%) | 72.77 | 8.00 | 5.85 |

NMR(δ/CDCl₃)

δ = 1.50~1.95(m, 14H, 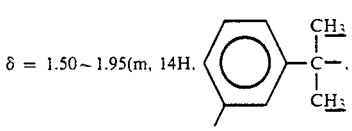),

—OCH₂CH₂CH₂O—), 2.15(s, 6H, 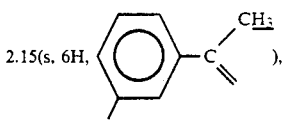), 4.04(s, 4H, —OCH₂CH₂CH₂O—), 5.07(s, 4H, 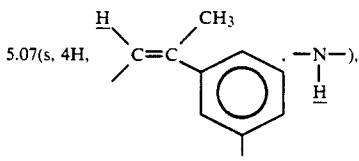, —N(H)—), 5.34(s, 2H, 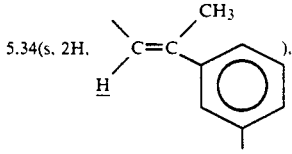), 7.29(s, 6H, 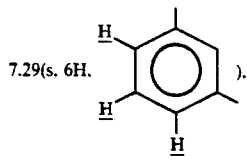), 7.47(s, 2H, 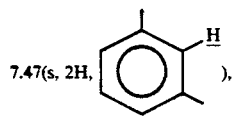),

EXAMPLE 4

The same procedure as in Example 2 was repeated except that 6.2 parts of ethylene glycol was replaced with 7.6 parts of 1,3-propanediol, thereby obtaining 41.7 parts of 1,3-bis[N-(4-isopropenyl-α,α-dimethylbenzyl)-carbamoyloxy]propane in the form of a colorless transparent liquid.

| Values of elemental analysis (as C<sub>29</sub>H<sub>38</sub>N<sub>2</sub>O<sub>4</sub>) | | | |
|---|---|---|---|
| | C | H | N |
| Found (%) | 72.98 | 8.13 | 5.53 |
| Calcd. (%) | 72.77 | 8.00 | 5.85 |

NMR(δ/CDCl₃)

δ = 1.50~1.95(m, 14H, 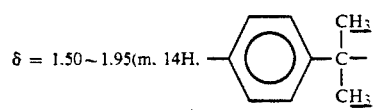

—OCH₂CH₂CH₂O—), 2.15(s, 6H, ), 4.04(s, 4H, —OCH₂CH₂CH₂O—), 5.08(s, 4H, 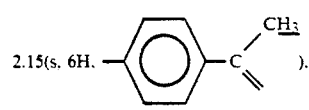), 5.39(s, 2H, ), 7.34(s, 8H, 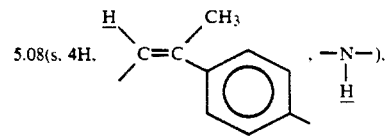),

EXAMPLE 5

The same procedure as in Example 1 was repeated except that 6.2 parts of ethylene glycol was replaced with 9.0 parts of 1,4-butanediol, thereby obtaining 44.4 parts of 1,4-bis[N-(3-isopropenyl-α,α-dimethylbenzyl)-carbamoyloxy]butane in the form of a colorless transparent liquid.

| Values of elemental analysis (as C<sub>30</sub>H<sub>40</sub>N<sub>2</sub>O<sub>4</sub>) | | | |
|---|---|---|---|
| | C | H | N |
| Found (%) | 72.88 | 8.23 | 5.47 |
| Calcd. (%) | 73.14 | 8.18 | 5.69 |

NMR(δ/CDCl₃)

δ = 1.45~1.80(m, 16H, 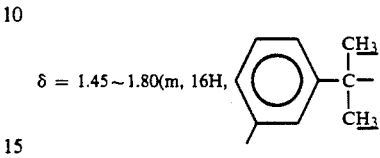

—OCH₂CH₂CH₂CH₂O—), 2.14(s, 6H, 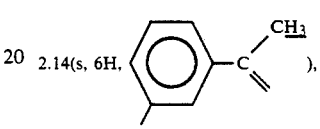), 3.99(s, 4H, —OCH₂CH₂CH₂CH₂O—), 5.07(s, 4H, 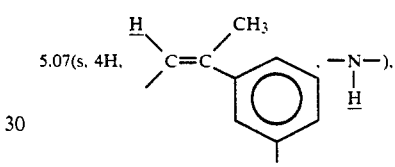), 5.33(s, 2H, 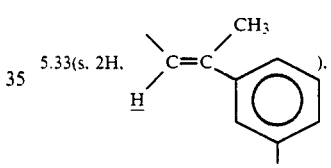), 7.29(s, 6H, 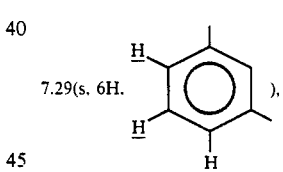), 7.48(s, 2H, 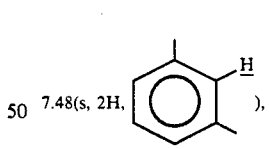),

EXAMPLE 6

The same procedure as in Example 2 was repeated except that 6.2 parts of ethylene glycol was replaced with 9.0 parts of 1,4-butanediol, thereby obtaining 43.9 parts of 1,4-bis[N-(4-isopropenyl-α,α-dimethylbenzyl)-carbamoyloxy]butane in the form of a colorless transparent liquid.

| Values of elemental analysis (as C<sub>30</sub>H<sub>40</sub>N<sub>2</sub>O<sub>4</sub>) | | | |
|---|---|---|---|
| | C | H | N |
| Found (%) | 73.29 | 7.96 | 5.73 |
| Calcd. (%) | 73.14 | 8.18 | 5.69 |

NMR(δ/CDCl₃)

δ = 1.45~1.80(m, 16H, 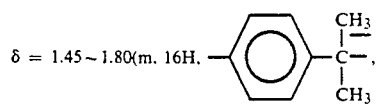

—OCH₂CH₂CH₂CH₂O—), 2.14(s, 6H, 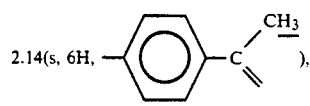), 3.99(s, 4H, —OCH₂CH₂CH₂CH₂O—), 5.07(s, 4H, 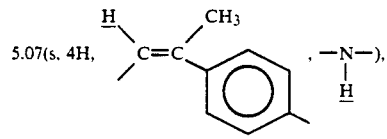, —N—),
                                      H 5.38(s, 2H, 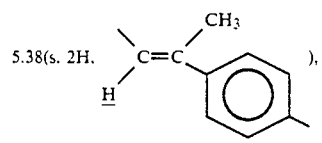), 7.35(s, 8H, 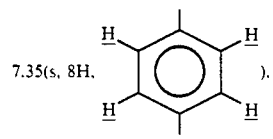).

EXAMPLE 7

The same procedure as in Example 1 was repeated except that 6.2 parts of ethylene glycol was replaced with 10.4 parts of 1,5-pentanediol, thereby obtaining 44.6 parts of 1,5-bis[N-(3-isopropenyl-α,α-dimethylbenzyl)carbamoyloxy]pentane in the form of a colorless transparent liquid.

| Values of elemental analysis (as C₃₁H₄₂N₂O₄) | | | |
|---|---|---|---|
| | C | H | N |
| Found (%) | 73.53 | 8.47 | 5.36 |
| Calcd. (%) | 73.49 | 8.35 | 5.53 |

NMR(δ/CDCl₃)

δ = 1.10~1.80(m, 18H, 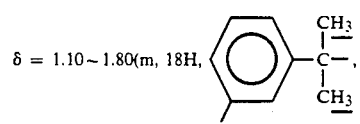

—OCH₂CH₂CH₂CH₂CH₂O—), 2.15(s, 6H, 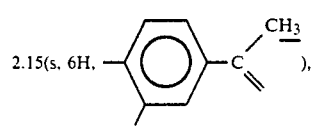), 3.96(s, 4H, —OCH₂CH₂CH₂CH₂CH₂O—), 5.07(s, 4H, 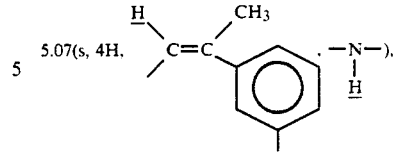, —N—),
                                      H 5.34(s, 2H, 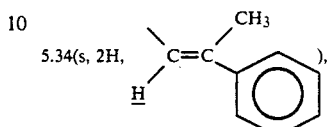), 7.28(s, 6H, 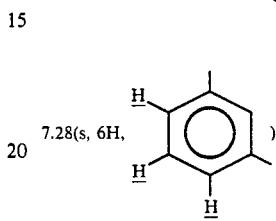), 7.48(s, 2H, 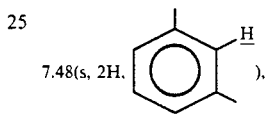),

EXAMPLE 8

The same procedure as in Example 2 was repeated except that 6.2 parts of ethylene glycol was replaced with 10.4 parts of 1,5-pentanediol, thereby obtaining 43.6 parts of 1,5-bis[N-(4-isopropenyl-α,α-dimethylbenzyl)carbamoyloxy]pentane in the form of a colorless transparent liquid.

| Values of elemental analysis (as C₃₁H₄₂N₂O₄) | | | |
|---|---|---|---|
| | C | H | N |
| Found (%) | 73.88 | 8.19 | 5.74 |
| Calcd. (%) | 73.49 | 8.35 | 5.53 |

NMR(δ/CDCl₃)

δ = 1.10~1.80(m, 18H, 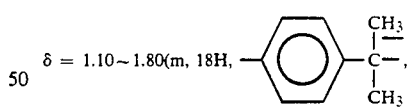

—OCH₂CH₂CH₂CH₂CH₂O—), 2.15(s, 6H, 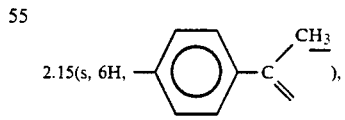), 3.96(s, 4H, —OCH₂CH₂CH₂CH₂CH₂O—), 5.08(s, 4H, 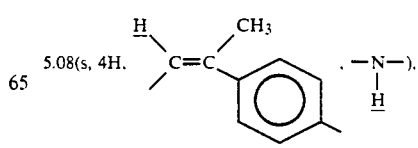, —N—),
                                      H 5.39(s, 2H, 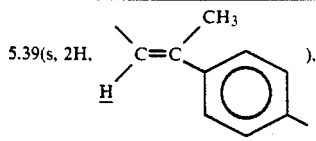), 7.35(s, 8H, 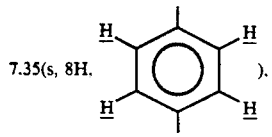).

EXAMPLE 9

The same procedure as in Example 1 was repeated except that 6.2 parts of ethylene glycol was replaced with 11.8 parts of 1,6-hexanediol, thereby obtaining 48.5 parts of 1,6-bis[N-(3-isopropenyl-α,α-dimethylbenzyl)-carbamoyloxy]-hexane in the form of a colorless transparent liquid.

| Values of elemental analysis (as $C_{32}H_{44}N_2O_4$) | | | |
|---|---|---|---|
| | C | H | N |
| Found (%) | 73.98 | 8.43 | 5.51 |
| Calcd. (%) | 73.81 | 8.52 | 5.38 |

NMR(δ/CDCl$_3$)

δ = 1.10~1.80(m, 20H, 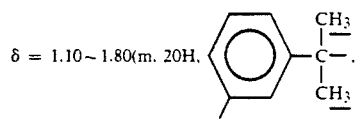,

—OCH$_2$CH$_2$CH$_2$CH$_2$CH$_2$CH$_2$O—), 2.15(s, 6H, 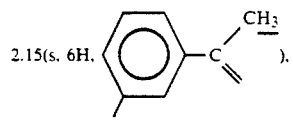), 3.95(s, 4H, —OCH$_2$CH$_2$CH$_2$CH$_2$CH$_2$CH$_2$O—), 5.07(s, 4H, 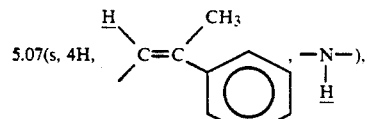, —N—), 5.34(s, 2H, 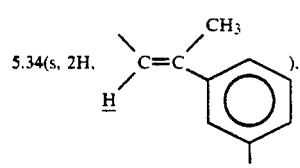), 7.28(s, 6H, 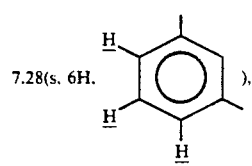), 7.48(s, 2H, 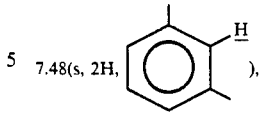),

EXAMPLE 10

The same procedure as in Example 2 was repeated except that 6.2 parts of ethylene glycol was replaced with 11.8 parts of 1,6-hexanediol, thereby obtaining 47.7 parts of 1,6-bis[N-(4-isopropenyl)-α,α-dimethylbenzyl)-carbamoyloxy]hexane in the form of a colorless transparent liquid.

| Values of elemental analysis (as $C_{32}H_{44}N_2O_4$) | | | |
|---|---|---|---|
| | C | H | N |
| Found (%) | 73.97 | 8.61 | 5.14 |
| Calcd. (%) | 73.81 | 8.52 | 5.38 |

NMR(δ/CDCl$_3$)

δ = 1.10~1.80(m, 20H, 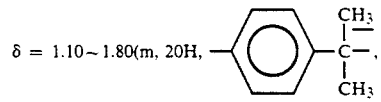,

—OCH$_2$CH$_2$CH$_2$CH$_2$CH$_2$CH$_2$O—), 2.15(s, 6H, 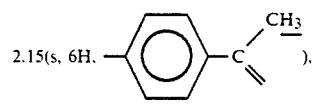), 3.95(s, 4H, —OCH$_2$CH$_2$CH$_2$CH$_2$CH$_2$CH$_2$O—), 5.08(s, 4H, 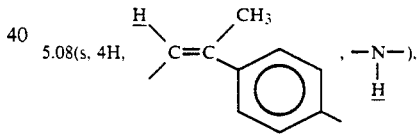, —N—), 5.39(s, 2H, 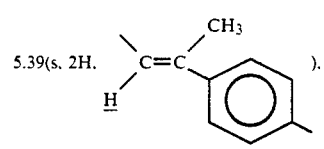), 7.35(s, 8H, 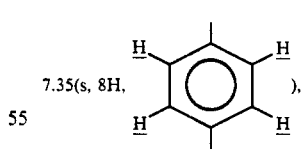),

EXAMPLE 11

The same procedure as in Example 1 was repeated except that 6.2 parts of ethylene glycol was replaced with 7.6 parts of 1,2-propanediol, thereby obtaining 43.1 parts of 1,2-bis[N-(3-isopropenyl-α,α-dimethylbenzyl)-carbamoyloxy]propane in the form of a colorless transparent liquid.

Values of elemental analysis (as $C_{29}H_{38}N_2O_4$)

| | C | H | N |
|---|---|---|---|
| Found (%) | 72.63 | 8.15 | 5.67 |
| Calcd. (%) | 72.77 | 8.00 | 5.85 |

NMR(δ/CDCl₃)

δ = 1.17(s, 3H, —OCH₂CHO—\|CH₃), 1.65(s, 12H, -C₆H₄-C(CH₃)₂-), 2.14(s, 6H, -C₆H₄-C(CH₃)=CH₂), 3.99(d, 2H, —OCH₂CHO—\|CH₃), 4.90(s, 1H, —OCH₂CHO—\|CH₃), 5.07(s, 4H, H₂C=C(CH₃)-C₆H₄-, —NH—), 5.34(s, 2H, H(CH₃)C=C-C₆H₄-), 7.27(s, 6H, C₆H₃), 7.47(s, 2H, C₆H₃).

EXAMPLE 12

The same procedure as in Example 2 was repeated except that 6.2 parts of ethylene glycol was replaced with 7.6 parts of 1,2-propanediol, thereby obtaining 44.8 parts of 1,2-bis[N-(4-isopropenyl-α,α-dimethylbenzyl)-carbamoyloxy]propane in the form of a colorless transparent liquid.

| Values of elemental analysis (as C₂₉H₃₈N₂O₄) | | | |
|---|---|---|---|
| | C | H | N |
| Found (%) | 72.69 | 8.15 | 5.72 |
| Calcd. (%) | 72.77 | 8.00 | 5.85 |

NMR(δ/CDCl₃)

δ = 1.17(s, 3H, —OCH₂CHO—\|CH₃).

1.65(s, 12H, -C₆H₄-C(CH₃)₂-), 2.15(s, 6H, -C₆H₄-C(CH₃)=CH₂), 3.99(d, 2H, —OCH₂CHO—\|CH₃), 4.90(s, 1H, —OCH₂CHO—\|CH₃), 5.08(s, 4H, H₂C=C(CH₃)-C₆H₄-, —NH—), 5.39(s, 2H, H(CH₃)C=C-C₆H₄-), 7.34(s, 8H, C₆H₄).

EXAMPLE 13

The same procedure as in Example 1 was repeated except that 6.2 parts of ethylene glycol was replaced with 9.0 parts of 1,3-butanediol, thereby obtaining 45.2 parts of 1,3-bis[N-(3-isopropenyl-α,α-dimethylbenzyl)-carbamoyloxy]butane in the form of a colorless transparent liquid.

| Values of elemental analysis (as C₃₀H₄₀N₂O₄) | | | |
|---|---|---|---|
| | C | H | N |
| Found (%) | 72.98 | 7.87 | 5.81 |
| Calcd. (%) | 73.14 | 8.18 | 5.69 |

NMR(δ/CDCl₃)

δ = 1.17(s, 3H, —OCH₂CH₂CHO—\|CH₃), 1.45~1.95(m, 14H, -C₆H₄-C(CH₃)₂-),

-continued

CH$_3$
|
—OCHCH$_2$CH$_2$O—), 2.14(s, 6H, [phenyl-C(CH$_3$)=CH$_2$ with CH$_3$ on ring]), CH$_3$
|
4.03(s, 2H, —OCH$_2$CH$_2$CHO—), CH$_3$
|
4.82(s, 1H, —OCH$_2$CH$_2$CHO—), 5.07(s, 4H, H\\C=C/CH$_3$—[phenyl]—N—),
           /      \\            |
                                H 5.34(s, 2H, \\C=C/CH$_3$—[phenyl]),
             /   \\
             H 7.28(s, 6H, [phenyl ring with H's]), 7.47(s, 2H, [phenyl with H]).

EXAMPLE 14

The same procedure as in Example 2 was replaced except that 6.2 parts of ethylene glycol was replaced with 9.0 parts of 1,3-butanediol, thereby obtaining 46.7 parts of 1,3-bis[N-(4-isopropenyl-α,α-dimethylbenzyl)-carbamoyloxy]butane in the form of a colorless transparent liquid.

| Values of elemental analysis (as C$_{30}$H$_{40}$N$_2$O$_4$) | | | |
|---|---|---|---|
| | C | H | N |
| Found (%) | 73.37 | 8.03 | 5.86 |
| Calcd. (%) | 73.14 | 8.18 | 5.69 |

NMR(δ/CDCl$_3$)

CH$_3$
|
δ = 1.17(s, 3H, —OCH$_2$CH$_2$CHO—),

CH$_3$  CH$_3$
|     |
1.45~1.95(m, 14H, —[phenyl]—C—, —OCHCH$_2$CH$_2$O—),
                    |
                    CH$_3$ 2.14(s, 6H, [phenyl-C(CH$_3$)=CH$_2$]), CH$_3$
|
4.03(s, 2H, —OCH$_2$CH$_2$CHO—), CH$_3$
|
4.82(s, 1H, —OCH$_2$CH$_2$CHO—), 5.08(s, 4H, H\\C=C/CH$_3$—[phenyl]—N—),
            /    \\              |
                                 H 5.39(s, 2H, \\C=C/CH$_3$—[phenyl]),
             /   \\
             H 7.35(s, 8H, [phenyl ring with H's]).

EXAMPLE 15

The same procedure as in Example 1 was repeated except that 6.2 parts of ethylene glycol was replaced with 9.0 parts of 2,3-butanediol, thereby obtaining 44.8 parts of 2,3-bis[N-(3-isopropenyl-α,α-dimethylbenzyl)-carbamoyloxy]butane in the form of a colorless transparent liquid.

| Values of elemental analysis (as C$_{30}$H$_{40}$N$_2$O$_4$) | | | |
|---|---|---|---|
| | C | H | N |
| Found (%) | 73.01 | 8.29 | 5.42 |
| Calcd. (%) | 73.14 | 8.18 | 5.69 |

NMR(δ/CDCl$_3$)

CH$_3$
|
δ = 1.15(s, 6H, —OCHCHO—),
|
CH$_3$

CH$_3$
|
1.45~1.95(m, 12H, [phenyl]—C—),
                    |
                    CH$_3$ 2.14(s, 6H, [phenyl-C(CH$_3$)=CH$_2$]), CH$_3$  CH$_3$
|     |
4.77(s, 2H, —OCHCHO—).

5.01(s, 2H, —NH—), 5.07(s, 4H, 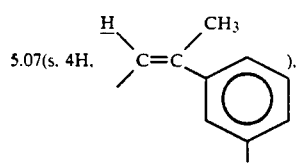), 5.34(s, 2H, 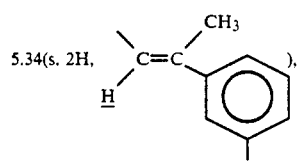), 7.27(s, 6H, 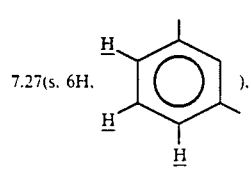), 7.48(s, 2H, 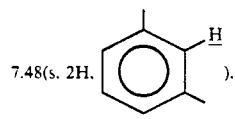).

EXAMPLE 16

The same procedure as in Example 2 was repeated except that 6.2 parts of ethylene glycol was replaced with 9.0 parts of 2,3-butanediol, thereby obtaining 42.9 parts of 2,3-bis[N-(4-isopropenyl-α,α-dimethylbenzyl)-carbamoyloxy]butane in the form of a colorless transparent liquid.

| Values of elemental analysis (as $C_{30}H_{40}N_2O_4$) | | | |
|---|---|---|---|
| | C | H | N |
| Found (%) | 73.44 | 8.09 | 5.47 |
| Calcd. (%) | 73.14 | 8.18 | 5.69 |

NMR(δ/CDCl₃)

δ = 1.15(s, 6H, —OCHCHO—),
  |
  CH₃

1.45~1.95(m, 12H, 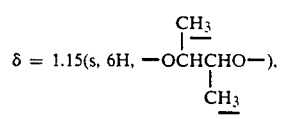), 2.14(s, 6H, 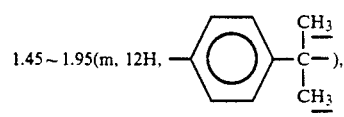), 4.77(s, 2H, —OCHCHO—),
        |  |
        CH₃ CH₃

5.02(s, 2H, —NH—), 5.08(s, 4H, 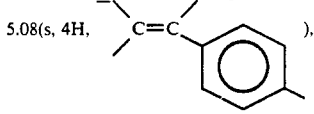), 5.39(s, 2H, 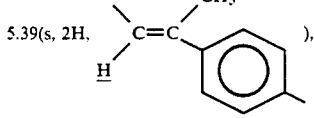), 7.35(s, 8H, 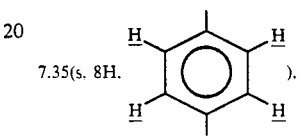).

EXAMPLE 17

The same procedure as in Example 1 was repeated except that 6.2 parts of ethylene glycol was replaced with 11.8 parts of 2,5-hexanediol, thereby obtaining 49.1 parts of 2,5-bis[N-(3-isopropenyl-α,α-dimethylbenzyl)-carbamoyloxy]hexane in the form of a colorless transparent liquid.

| Values of elemental analysis (as $C_{32}H_{44}N_2O_4$) | | | |
|---|---|---|---|
| | C | H | N |
| Found (%) | 73.98 | 8.36 | 5.14 |
| Calcd. (%) | 73.81 | 8.52 | 5.38 |

NMR(δ/CDCl₃)

δ = 0.85~1.75(m, 22H, —OCHCH₂CH₂CHO—),
                      |          |
                      CH₃        CH₃

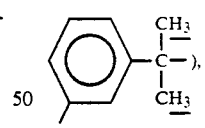, 2.14(s, 6H, 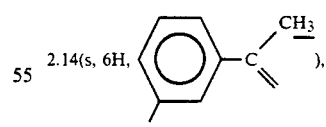), 4.71(s, 2H, —OCHCH₂CH₂CHO—),
            |          |
            CH₃        CH₃

5.06(s, 4H, 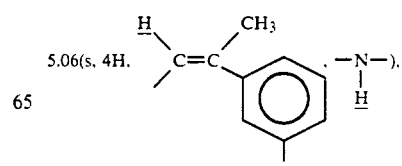), 5.34(s, 2H, 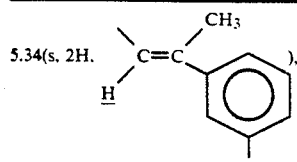

7.28(m, 6H, 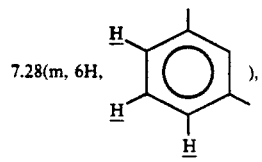

7.47(s, 2H, 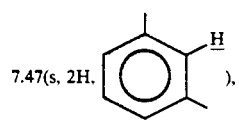

EXAMPLE 18

The same procedure as in Example 2 was repeated except that 6.2 parts of ethylene glycol was replaced with 11.8 parts of 2,5-hexanediol, thereby obtaining 47.9 parts of 2,5-bis[N-(4-isopropenyl-α,α-dimethylbenzyl)-carbamoyloxy]hexane in the form of a colorless transparent liquid.

| Values of elemental analysis (as $C_{32}H_{44}N_2O_4$) | | | |
|---|---|---|---|
| | C | H | N |
| Found (%) | 74.03 | 8.77 | 5.28 |
| Calcd. (%) | 73.81 | 8.52 | 5.38 |

NMR(δ/CDCl₃)

$\delta = 0.85 \sim 1.75$(m, 22H, 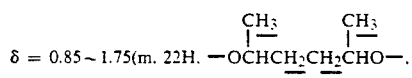

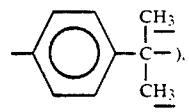

2.14(s, 6H, 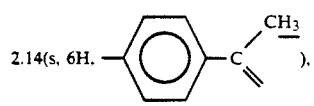

4.71(s, 2H, 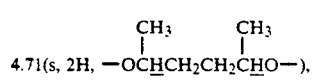

5.08(s, 4H, 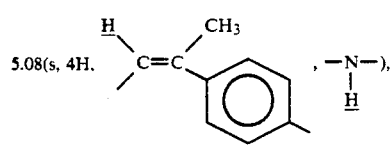

5.39(s, 2H, 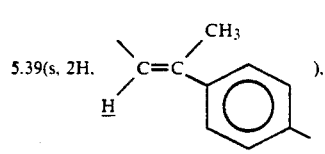

7.34(m, 8H, 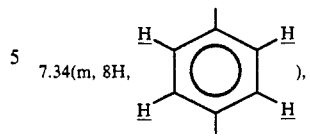

EXAMPLE 19

The same procedure as in Example 1 was repeated except that 6.2 parts of ethylene glycol was replaced with 10.6 parts of diethylene glycol, thereby obtaining 47.4 parts of bis[2-(N-(3-isopropenyl-α,α-dimethylbenzyl)carbamoyloxy)ethyl] ether in the form of a colorless transparent liquid.

| Values of elemental analysis (as $C_{30}H_{40}N_2O_5$) | | | |
|---|---|---|---|
| | C | H | N |
| Found (%) | 70.66 | 7.72 | 5.68 |
| Calcd. (%) | 70.84 | 7.93 | 5.51 |

NMR(δ/CDCl₃)

$\delta = 1.66$(s, 12H, 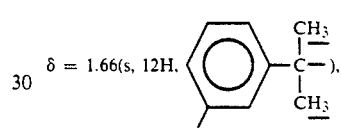

2.14(s, 6H, 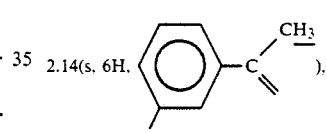

3.64(s, 4H, —OCH₂CH₂OCH₂CH₂O—), 4.15(s, 4H, —OCH₂CH₂OCH₂CH₂O—), 5.07(s, 2H, 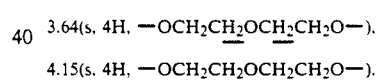

5.25(s, 2H, 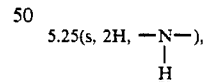

5.34(s, 2H, 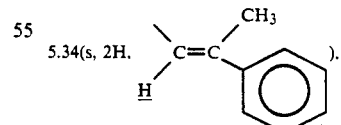

7.30(s, 6H, 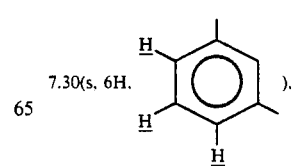

7.48(s, 2H, 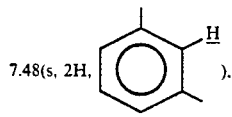).

EXAMPLE 20

The same procedure as in Example 2 was repeated except that 6.2 parts of ethylene glycol was replaced with 10.6 parts of diethylene glycol, thereby obtaining 47.6 parts of bis[2-(N-(4-isopropenyl-α,α-dimethylbenzyl)carbamoyloxy)ethyl] ether in the form of a colorless transparent liquid.

| Values of elemental analysis (as $C_{30}H_{40}N_2O_5$) | | | |
|---|---|---|---|
| | C | H | N |
| Found (%) | 70.79 | 7.98 | 5.38 |
| Calcd. (%) | 70.84 | 7.93 | 5.51 |

NMR(δ/CDCl₃)

δ = 1.66(s, 12H, 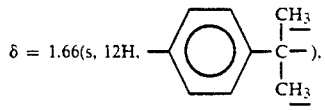), 2.15(s, 6H, 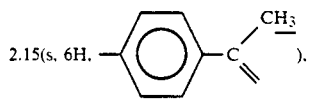), 3.64(s, 4H, —OCH₂CH₂OCH₂CH₂O—), 4.15(s, 4H, —OCH₂CH₂OCH₂CH₂O—), 5.08(s, 2H, 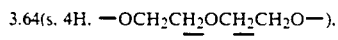), 5.25(s, 2H, —N—),
            |
            H 5.39(s, 2H, 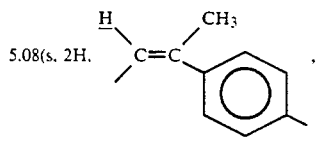), 7.36(s, 8H, 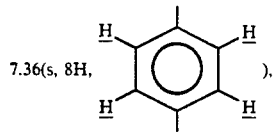).

EXAMPLE 21

The same procedure as in Example 1 was repeated except that 6.2 parts of ethylene glycol was replaced with 10.4 parts of neopentyl glycol, thereby obtaining 46.9 parts of 2,2-dimethyl-1,3-bis[N-(3-isopropenyl-α,α-dimethylbenzyl)carbamoyloxy]propane in the form of a colorless transparent liquid.

| Values of elemental analysis (as $C_{31}H_{42}N_2O_4$) | | | |
|---|---|---|---|
| | C | H | N |
| Found (%) | 73.38 | 8.34 | 5.74 |
| Calcd. (%) | 73.49 | 8.35 | 5.53 |

NMR(δ/CDCl₃)

δ = 0.89(s, 6H, 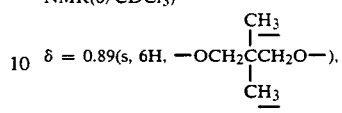), 1.66(s, 12H, 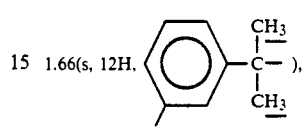), 2.14(s, 6H, 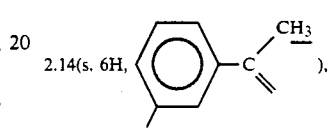), 3.79(s, 4H, 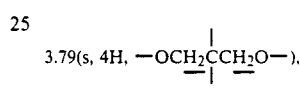), 5.07(s, 2H, 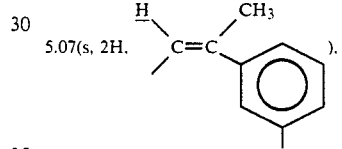), 5.14(s, 2H, —N—),
            |
            H 5.32(s, 2H, 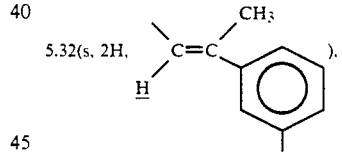), 7.29(s, 6H, 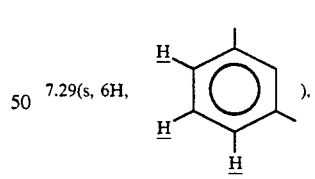), 7.47(s, 2H, 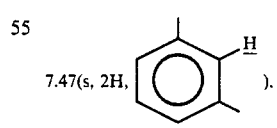).

EXAMPLE 22

The same procedure as in Example 2 was repeated except that 6.2 parts of ethylene glycol was replaced with 10.4 parts of neopentyl glycol, thereby obtaining 48.1 parts of 2,2-dimethyl-1,3-bis[N-(4-isopropenyl-α,α-dimethylbenzyl)carbamoyloxy]propane in the form of a colorless transparent liquid.

| Values of elemental analysis (as $C_{31}H_{42}N_2O_4$) | | | |
|---|---|---|---|
| | C | H | N |
| Found (%) | 73.18 | 8.42 | 5.71 |
| Calcd. (%) | 73.49 | 8.35 | 5.53 |

NMR($\delta$/CDCl$_3$)

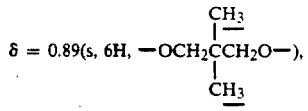
$\delta = 0.89$(s, 6H, —OCH$_2$CCH$_2$O—),

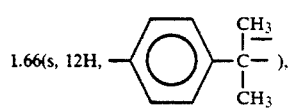
1.66(s, 12H,

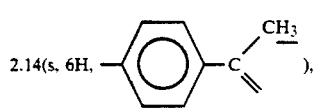
2.14(s, 6H,

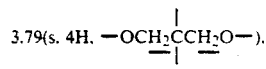
3.79(s, 4H, —OCH$_2$CCH$_2$O—).

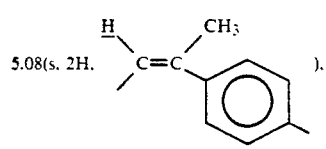
5.08(s, 2H,

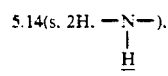
5.14(s, 2H, —N—),

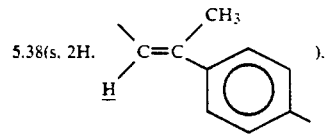
5.38(s, 2H,

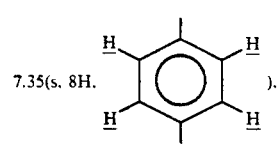
7.35(s, 8H,

EXAMPLE 23

The same procedure as in Example 1 was repeated except that 6.2 parts of ethylene glycol was replaced with 11.8 parts of 3-methyl-1,5-pentanediol, thereby obtaining 47.7 parts of 3-methyl-1,5-bis[N-(3-isopropenyl-α,α-dimethylbenzyl)carbamoyloxy]pentane in the form of a colorless transparent liquid.

| Values of elemental analysis (as $C_{32}H_{44}N_2O_4$) | | | |
|---|---|---|---|
| | C | H | N |
| Found (%) | 73.67 | 8.74 | 5.36 |
| Calcd. (%) | 73.81 | 8.52 | 5.38 |

NMR($\delta$/CDCl$_3$)

$\delta = 0.90$(s, 3H, OCH$_2$CH$_2$CHCH$_2$CH$_2$O).

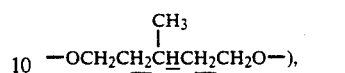
1.10~2.00(m, 19H,

—OCH$_2$CH$_2$CHCH$_2$CH$_2$O—),

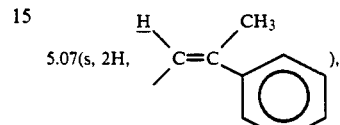
4.00(s, 4H, OCH$_2$CH$_2$CHCH$_2$CH$_2$O).

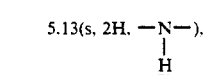
5.07(s, 2H,

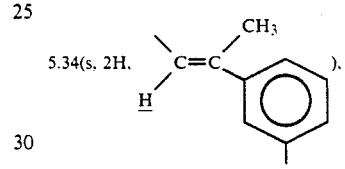

5.13(s, 2H, —N—),

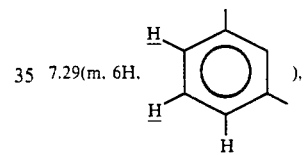
5.34(s, 2H,

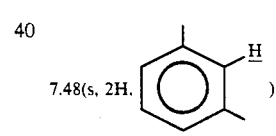
7.29(m, 6H, 7.48(s, 2H,

EXAMPLE 24

The same procedure as in Example 2 was repeated except that 6.2 parts of ethylene glycol was replaced with 11.8 parts of 3-methyl-1,5-pentanediol, thereby obtaining 46.8 parts of 3-methyl-1,5-bis[N-(4-isopropenyl-α,α-dimethylbenzyl)carbamoyloxy]pentane in the form of a colorless transparent liquid.

| Values of elemental analysis (as $C_{32}H_{44}N_2O_4$) | | | |
|---|---|---|---|
| | C | H | N |
| Found (%) | 73.93 | 8.76 | 5.24 |
| Calcd. (%) | 73.81 | 8.52 | 5.38 |

NMR($\delta$/CDCl$_3$)

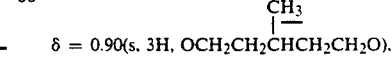
$\delta = 0.90$(s, 3H, OCH$_2$CH$_2$CHCH$_2$CH$_2$O).

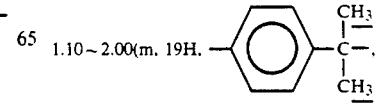
1.10~2.00(m, 19H,

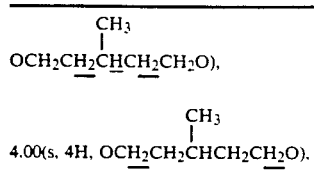
4.00(s, 4H, OCH₂CH₂CHCH₂CH₂O),

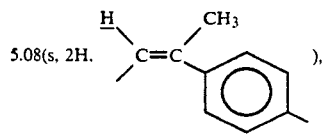
5.08(s, 2H, ...),

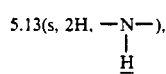
5.13(s, 2H, —N—),
         H

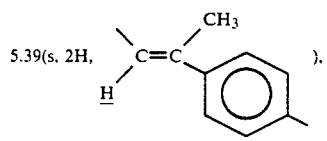
5.39(s, 2H, ...),

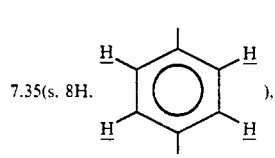
7.35(s, 8H, ...),

EXAMPLE 25

The same procedure as in Example 1 was repeated except that 6.2 parts of ethylene glycol was replaced with 13.4 parts of dipropylene glycol, thereby obtaining 49.7 parts of bis[(N-(3-isopropenyl-α,α-dimethylbenzyl)carbamoyloxy(isopropyl)] ether in the form of a colorless transparent liquid.

| Values of elemental analysis (as C₃₂H₄₄N₂O₅) | | | |
|---|---|---|---|
| | C | H | N |
| Found (%) | 71.78 | 8.14 | 5.06 |
| Calcd. (%) | 71.61 | 8.26 | 5.22 |

NMR(δ/CDCl₃)
δ = 1.16(d, 6H, OCHCH₂OCH₂OCH₂CHO).
                    |              |
                    CH₃          CH₃

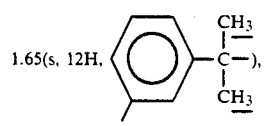
1.65(s, 12H, ...),

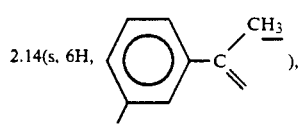
2.14(s, 6H, ...),

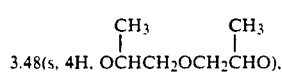
3.48(s, 4H, OCHCH₂OCH₂CHO),
     CH₃       CH₃

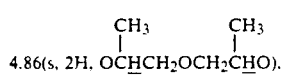
4.86(s, 2H, OCHCH₂OCH₂CHO),
     CH₃       CH₃

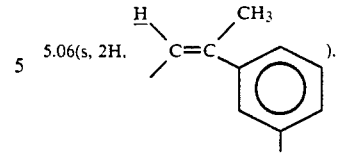
5.06(s, 2H, ...),

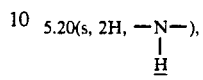
5.20(s, 2H, —N—),
         H

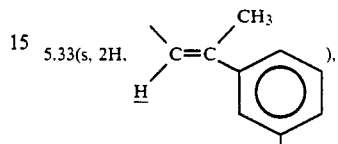
5.33(s, 2H, ...),

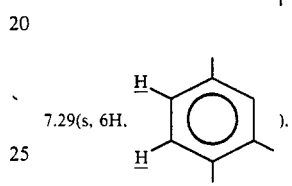
7.29(s, 6H, ...),

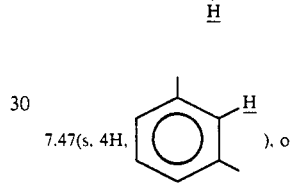
7.47(s, 4H, ...), or

δ = 1.16(d, 6H, OCH₂CHOCHCH₂O).
                    |      |
                    CH₃  CH₃

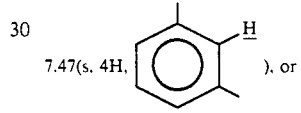
1.65(s, 12H, ...), 2.14(s, 6H, ...),

CH₃ CH₃
          |   |
3.48(s, 2H, OCH₂CHOCHCH₂O),

CH₃ CH₃
          |   |
3.93(s, 4H, OCH₂CHOCHCH₂O), 5.06(s, 2H, ...), 5.20(s, 2H, —N—),
         H

-continued 5.33(s, 2H, 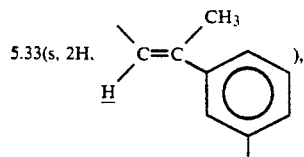), 7.29(s, 6H, 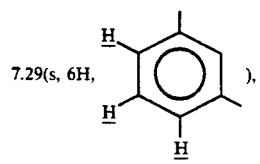), 7.47(s, 4H, 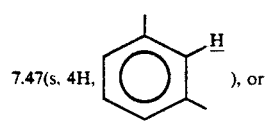), or δ = 1.16(d, 6H, OCHCH₂OCHCH₂O), 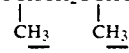
   |         |
   CH₃      CH₃

1.65(s, 12H, 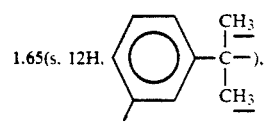), 2.14(s, 6H, 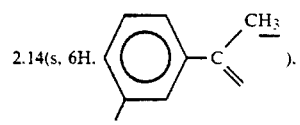),

CH₃     CH₃
      |       |
3.48(s, 3H, OCHCH₂OCHCH₂O), 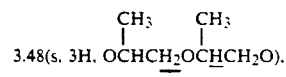

CH₃     CH₃
      |       |
3.93(s, 2H, OCHCH₂OCHCH₂O), 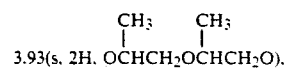

CH₃     CH₃
      |       |
4.86(s, 1H, OCHCH₂OCHCH₂O), 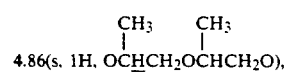

5.06(s, 2H, 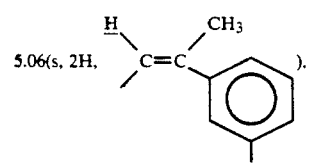), 5.20(s, 2H, 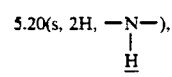), 5.33(s, 2H, 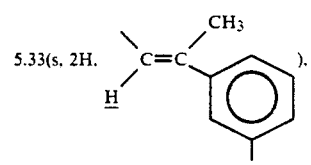).

-continued 7.29(s, 6H, 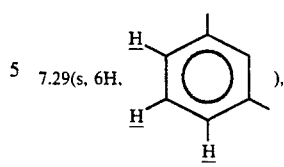), 7.47(s, 4H, 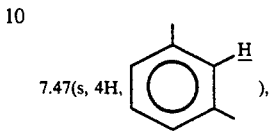),

EXAMPLE 26

The same procedure as in Example 2 was repeated except that 6.2 parts of ethylene glycol was replaced with 13.4 parts of dipropylene glycol, thereby obtaining 50.6 parts of bis[(N-(4-isopropenyl-α,α-dimethylbenzyl)carbamoyloxy)isopropyl] ether in the form of a colorless transparent liquid (a mixture is isomers).

| Values of elemental analysis (as $C_{32}H_{44}N_2O_5$) | | | |
|---|---|---|---|
| | C | H | N |
| Found (%) | 71.77 | 8.05 | 5.38 |
| Calcd. (%) | 71.61 | 8.26 | 5.22 |

NMR(δ/CDCl₃)
      CH₃     CH₃
      |       |
δ=1.16(d, 6H, OCHCH₂OCH₂CHO).

1.65(s, 12H, 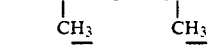), 2.14(s, 6H, 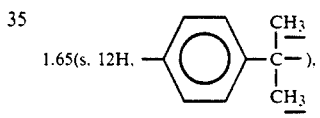),

CH₃     CH₃
      |       |
3.48(s, 4H, OCHCH₂OCH₂CHO), 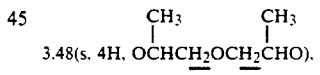

CH₃     CH₃
      |       |
4.86(s, 2H, OCHCH₂OCH₂CHO), 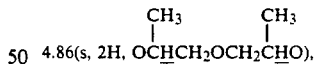

5.07(s, 2H, 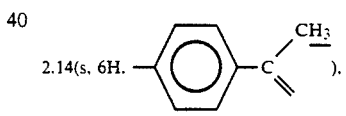), 5.20(s, 2H, 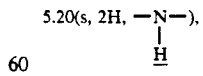), 5.39(s, 2H, 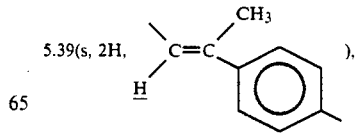),

-continued 7.35(s, 8H, 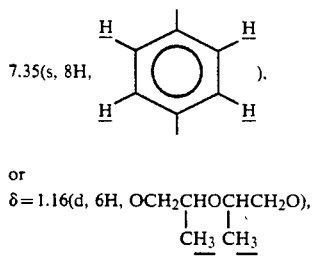 ), or

δ=1.16(d, 6H, OCH₂CHOCHCH₂O),
              |      |
              CH₃   CH₃

1.65(s, 12H, 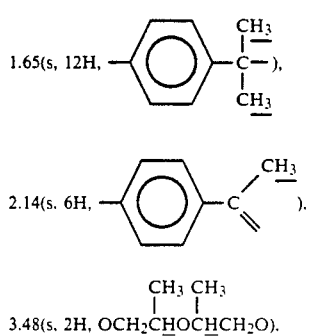 ), 2.14(s, 6H, 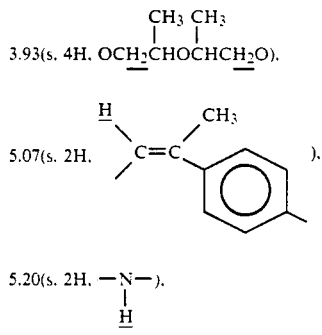 ), 3.48(s, 2H, OCH₂CHOCHCH₂O).
             |     |
             CH₃  CH₃

3.93(s, 4H, OCH₂CHOCHCH₂O).
             |    |
             CH₃ CH₃

5.07(s, 2H, 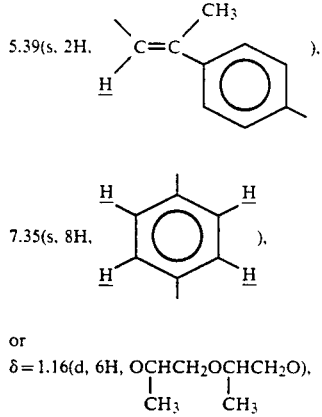 ), 5.20(s, 2H, —N— ),
              |
              H 5.39(s, 2H, 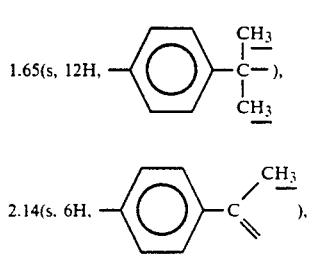 ), 7.35(s, 8H, same phenyl ), or δ=1.16(d, 6H, OCHCH₂OCHCH₂O),
              |      |
              CH₃   CH₃

1.65(s, 12H, same gem-dimethyl ), 2.14(s, 6H, same isopropenyl ),

-continued 3.48(s, 3H, OCHCH₂OCHCH₂O). 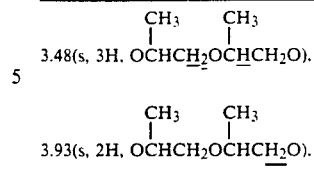

3.93(s, 2H, OCHCH₂OCHCH₂O). 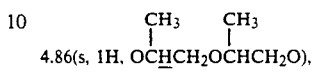

4.86(s, 1H, OCHCH₂OCHCH₂O), 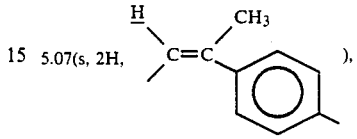

5.07(s, 2H, 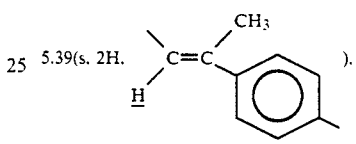 ), 5.20(s, 2H, —N— ). 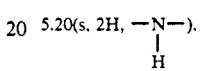
              |
              H 5.39(s, 2H, 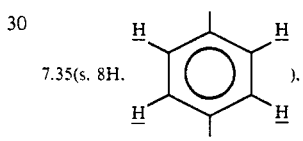 ), 7.35(s, 8H, phenyl ),

EXAMPLE 27

The same procedure as in Example 1 was repeated except that 6.2 parts of ethylene glycol was replaced with 15.0 parts of triethylene glycol, thereby obtaining 49.5 parts of bis[2-(N-(3-isopropenyl-α,α-dimethylbenzyl)carbamoyloxy)ethoxy]ethane in the form of a colorless transparent liquid.

| Values of elemental analysis (as C₃₂H₄₄N₂O₆) | | | |
|---|---|---|---|
|  | C | H | N |
| Found (%) | 69.62 | 8.31 | 4.93 |
| Calcd. (%) | 69.54 | 8.02 | 5.07 |

NMR(δ/CDCl₃)

δ=1.66(s, 12H, 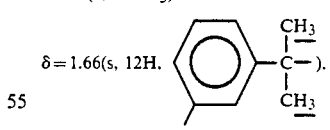 ), 2.15(s, 6H, 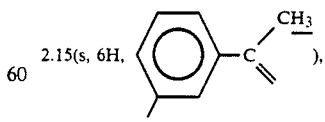 ), 3.65(s, 8H, OCH₂CH₂OCH₂CH₂OCH₂CH₂O). 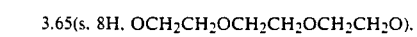

4.15(s, 4H, OCH₂CH₂OCH₂CH₂OCH₂CH₂O). 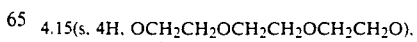

5.07(s, 2H, 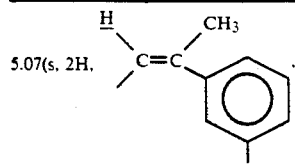

5.30(s, 2H, —N—).
              |
              H 5.34(s, 2H, 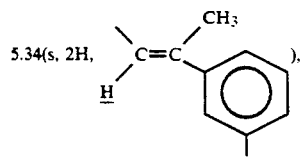

7.30(s, 6H, 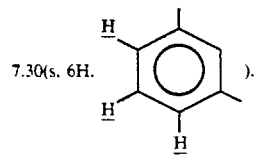

7.48(s, 2H, 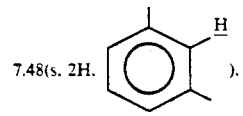

EXAMPLE 28

The same procedure as in Example 2 was repeated except that 6.2 parts of ethylene glycol was replaced with 15.0 parts of triethylene glycol, thereby obtaining 51.5 parts of bis[2-(N-(4-isopropenyl-α,α-dimethylbenzyl)carbamoyloxy)ethoxy]ethane in the form of a colorless transparent liquid.

| Values of elemental analysis (as C$_{32}$H$_{44}$N$_2$O$_6$) | | | |
|---|---|---|---|
| | C | H | N |
| Found (%) | 69.61 | 8.29 | 5.09 |
| Calcd. (%) | 69.54 | 8.02 | 5.07 |

NMR(δ/CDCl$_3$)

δ = 1.66(s, 12H, 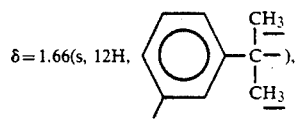

2.15(s, 6H, 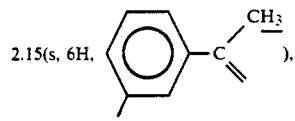

3.65(s, 8H, OCH$_2$CH$_2$OCH$_2$CH$_2$OCH$_2$CH$_2$O).

4.15(s, 4H, OCH$_2$CH$_2$OCH$_2$CH$_2$OCH$_2$CH$_2$O), 5.08(s, 2H, 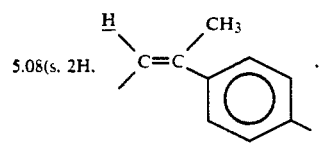

5.30(s, 2H, —N—),
              |
              H 5.39(s, 2H, 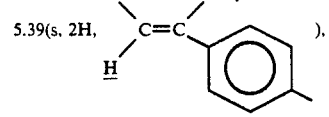

7.36(s, 8H, 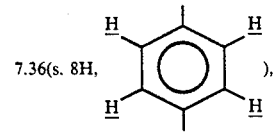

EXAMPLE 29

The same procedure as in Example 1 was repeated except that 6.2 parts of ethylene glycol was replaced with 9.0 parts of 1,2-butanediol, thereby obtaining 43.4 parts of 1,2-bis[N-(3-isopropenyl-α,α-dimethylbenzyl)carbamoyloxy]butane in the form of a colorless transparent liquid.

| Values of elemental analysis (as C$_{30}$H$_{40}$N$_2$O$_4$) | | | |
|---|---|---|---|
| | C | H | N |
| Found (%) | 72.98 | 8.34 | 5.47 |
| Calcd. (%) | 73.14 | 8.18 | 5.69 |

NMR(δ/CDCl$_3$)

δ = 0.90(s, 3H, OCH$_2$CHO   ),
                    |
                    CH$_2$CH$_3$ 1.37~1.82(m, 14H, OCH$_2$CHO
                     |
                     CH$_2$CH$_3$

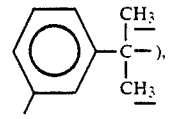

2.14(s, 6H, 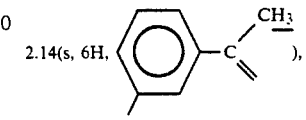

CH$_2$CH$_3$
         |
4.03(d, 2H, OCH$_2$CHO   ),

CH$_2$CH$_3$
         |
4.78(s, 1H, OCH$_2$CHO   ), 5.07(s, 4H. 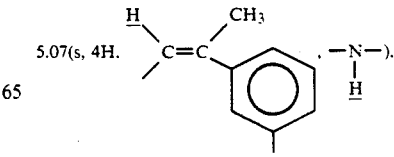  —N—).
                                    |
                                    H 5.34(s, 2H, 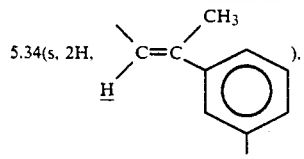

7.29(s, 6H, 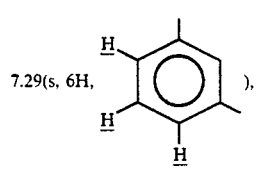), 7.48(s, 2H, 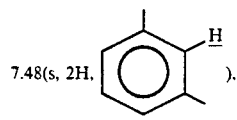).

EXAMPLE 30

The same procedure as in Example 2 was repeated except that 6.2 parts of ethylene glycol was replaced with 9.0 parts of 1,2-butanediol, thereby obtaining 46.4 parts of 1,2-bis[N-(4-isopropenyl-α,α-dimethylbenzyl)-carbamoyloxy]butane in the form of a colorless transparent liquid.

| Values of elemental analysis (as $C_{30}H_{40}N_2O_4$) | | | |
|---|---|---|---|
| | C | H | N |
| Found (%) | 73.18 | 8.07 | 5.43 |
| Calcd. (%) | 73.14 | 8.18 | 5.69 |

NMR(δ/CDCl$_3$)

δ = 0.90(s, 3H, 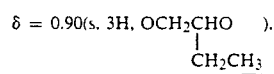).

1.37~1.82(m, 14H, 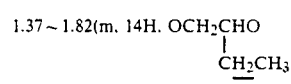

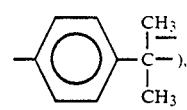

2.14(s, 6H, 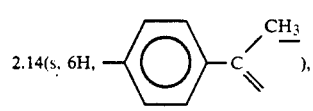), 4.03(d, 2H, 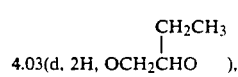), 4.78(s, 1H, ).

5.08(s, 4H, 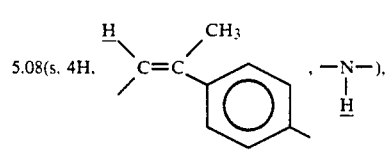).

5.39(s, 2H, 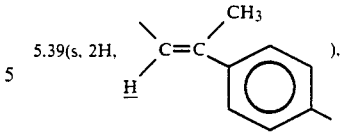).

7.35(s, 8H, 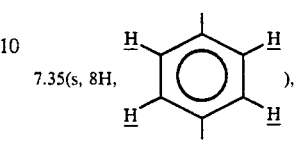),

EXAMPLE 31

The same procedure as in Example 1 was repeated except that 6.2 parts of ethylene glycol was replaced with 14.6 parts of 2-ethyl-1,3-hexanediol, thereby obtaining 50.4 parts of 2-ethyl-1,3-bis[N-(3-isopropenyl-α,α-dimethylbenzyl)carbamoyloxy]hexane in the form of a colorless transparent liquid.

| Values of elemental analysis (as $C_{34}H_{48}N_2O_4$) | | | |
|---|---|---|---|
| | C | H | N |
| Found (%) | 74.56 | 8.77 | 5.04 |
| Calcd. (%) | 74.42 | 8.82 | 5.10 |

NMR(δ/CDCl$_3$)

δ = 0.50~1.80(m, 25H, 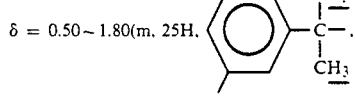

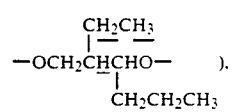).

2.14(s, 6H, 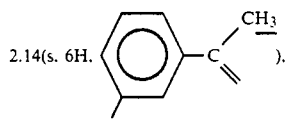).

3.94(d, 2H, 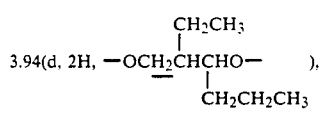), 4.80(s, 1H, 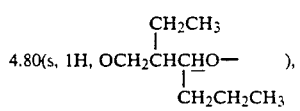), 5.06(s, 4H, 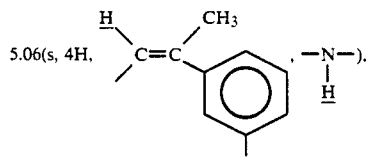).

5.33(s, 2H, 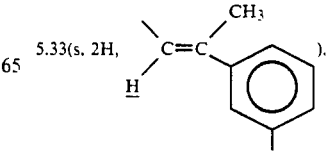).

7.29(s, 6H, 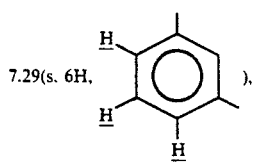), 7.47(s, 2H, 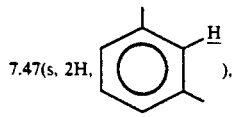),

EXAMPLE 32

The same procedure as in Example 2 was repeated except that 6.2 parts of ethylene glycol was replaced with 14.6 parts of 2-ethyl-1,3-hexanediol, thereby obtaining 51.1 parts of 2-ethyl-1,3-bis[N-(4-isopropenyl-α,α-dimethylbenzyl)carbamoyloxy]hexane in the form of a colorless transparent liquid.

| Values of elemental analysis (as $C_{34}H_{48}N_2O_4$) | | | |
|---|---|---|---|
| | C | H | N |
| Found (%) | 74.47 | 8.73 | 5.16 |
| Calcd. (%) | 74.42 | 8.82 | 5.10 |

NMR(δ/CDCl₃)

δ = 0.50~1.80(m, 25H, 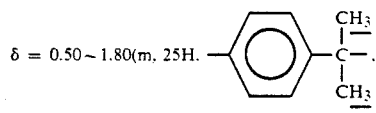,

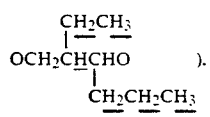 ), 2.14(s, 6H, 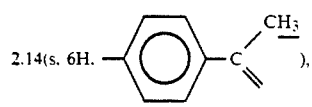), 3.94(d, 2H, 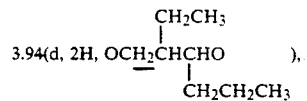), 4.80(s, 1H, 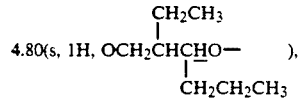), 5.07(s, 4H, 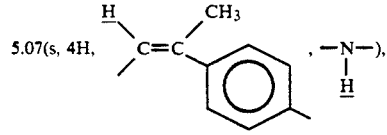), 5.38(s, 2H, 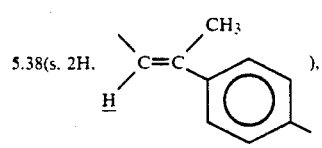), 7.35(s, 8H, 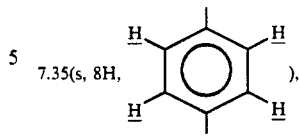),

EXAMPLE 33

The same procedure as in Example 1 was repeated except that 6.2 parts of ethylene glycol was replaced with 30.4 parts of 3,9-bis(1,1-dimethyl-2-hydroxyethyl)-2,4,8,10-tetraoxaspiro(5,5)undecane, thereby obtaining 66.7 parts of 3,9-bis[1,1-dimethyl-2-(N-(3-isopropenyl-α,α-dimethylbenzyl)carbamoyloxy)ethyl]-2,4,8,10-tetraoxaspiro (5,5)undecane in the form of a colorless transparent liquid.

| Values of elemental analysis (as $C_{41}H_{58}N_2O_8$) | | | |
|---|---|---|---|
| | C | H | N |
| Found (%) | 69.56 | 8.34 | 3.72 |
| Calcd. (%) | 69.66 | 8.27 | 3.96 |

NMR(δ/CDCl₃)

δ = 0.92(s, 12H, 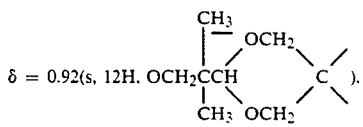), 1.66(s, 12H, 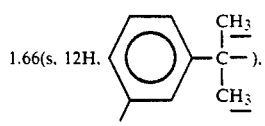), 2.15(s, 6H, 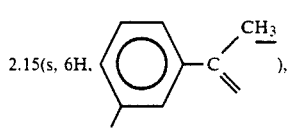), 3.67(s, 8H, 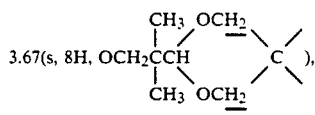), 3.83(s, 4H, 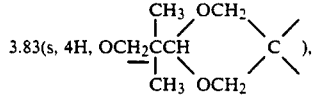), 4.32(s, 2H, 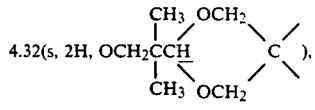), 5.09(s, 4H, 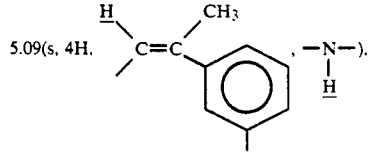), 5.35(s, 2H, 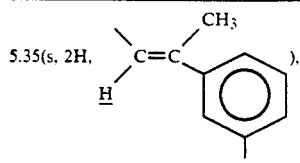

7.31(s, 6H, 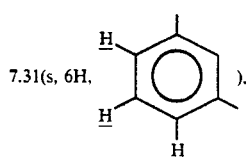

7.50(s, 2H, 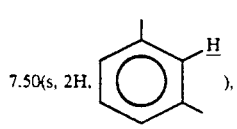

EXAMPLE 34

The same procedure as in Example 2 was repeated except that 6.2 parts of ethylene glycol was replaced with 30.4 parts of 3,9-bis(1,1-dimethyl-2-hydroxyethyl)-2,4,8,10-tetraoxaspiro(5,5)undecane, thereby obtaining 63.4 parts of 3,9-bis[1,1-dimethyl-2-(N-(4-isopropenyl-α,α-dimethylbenzyl)carbamoyloxy)ethyl]-2,4,8,10-tetraoxaspiro (5,5)undecane in the form of a colorless transparent liquid.

| Values of elemental analysis (as $C_{41}H_{58}N_2O_8$) | | | |
|---|---|---|---|
| | C | H | N |
| Found (%) | 69.73 | 8.48 | 3.75 |
| Calcd. (%) | 69.66 | 8.27 | 3.96 |

NMR($\delta$/CDCl$_3$)

$\delta$ = 0.92(s, 12H, 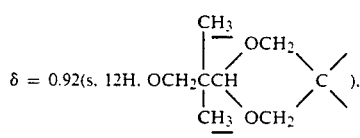

1.66(s, 12H, 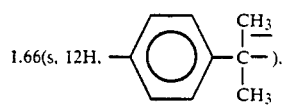

2.15(s, 6H, 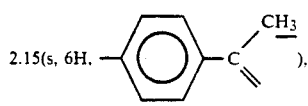

3.67(s, 8H, 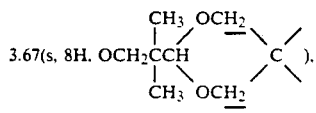

3.83(s, 4H, 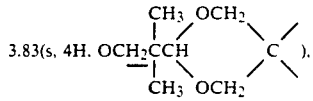

4.32(s, 2H, 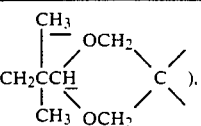

5.10(s, 4H, 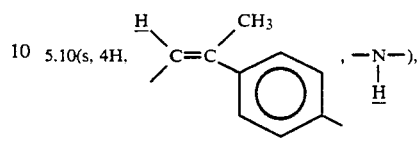, —N—),
                                    H 5.40(s, 2H, 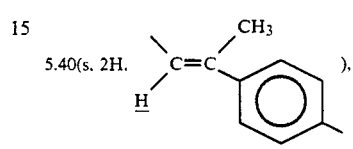

7.36(s, 8H, 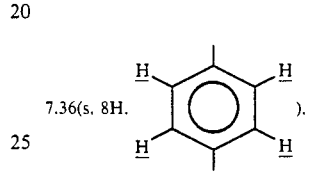

EXAMPLE 35

The same procedure as in Example 1 was repeated except that 6.2 parts of ethylene glycol was replaced with 11.6 parts of 1,4-cyclohexanediol, thereby obtaining 48.2 parts of 1,4-bis[N-(3-isopropenyl-α,α-dimethylbenzyl)carbamoyloxy]cyclohexane in the form of a colorless transparent liquid.

| Values of elemental analysis (as $C_{32}H_{42}N_2O_4$) | | | |
|---|---|---|---|
| | C | H | N |
| Found (%) | 74.23 | 8.05 | 5.62 |
| Calcd. (%) | 74.10 | 8.16 | 5.40 |

NMR($\delta$/CDCl$_3$)

$\delta$=0.90~2.00(m, 20H, 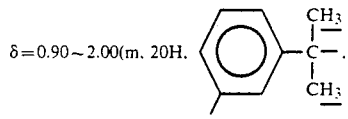

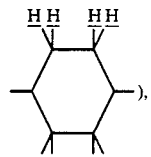

2.15(d, 6H, 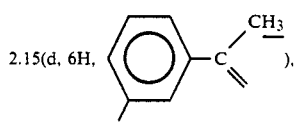

4.63(s, 2H, 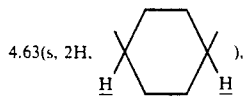

-continued 4.95~5.15(m, 4H, 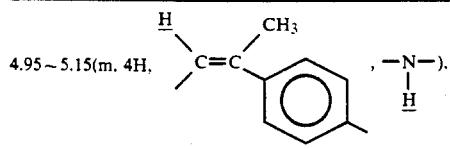, —N—), 5.33(d, 2H, 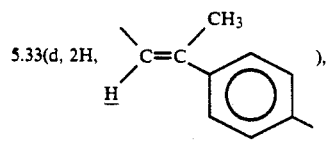), 7.20~7.55(m, 8H, 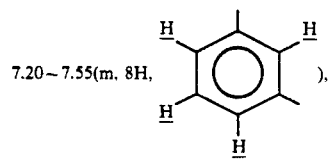),

EXAMPLE 36

The same procedure as in Example 2 was repeated except that 6.2 parts of ethylene glycol was replaced with 11.6 parts of 1,4-cyclohexanediol, thereby obtaining 46.7 parts of 1,4-bis[N-(4-isopropenyl-α,α-dimethylbenzyl)carbamoyloxy]cyclohexane in the form of a colorless transparent liquid.

| Values of elemental analysis (as $C_{32}H_{42}N_2O_4$) | | | |
|---|---|---|---|
| | C | H | N |
| Found (%) | 74.35 | 8.32 | 5.29 |
| Calcd. (%) | 74.10 | 8.16 | 5.40 |

NMR(δ/CDCl₃)

δ=0.90~2.00(m, 20H, 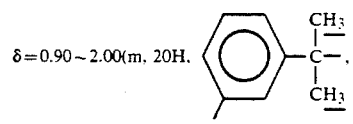,

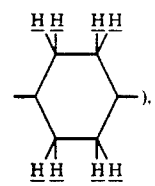), 2.15(d, 6H, 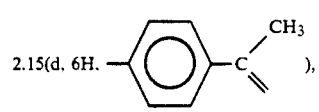), 4.63(s, 2H, 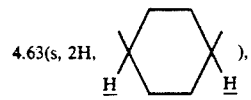), 4.95~5.15(m, 4H, 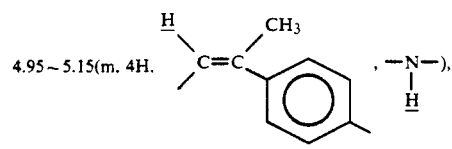, —N—), -continued 5.39(d, 2H, 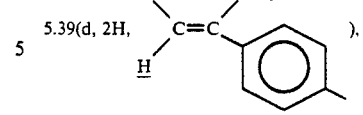), 7.29~7.51(m, 8H, 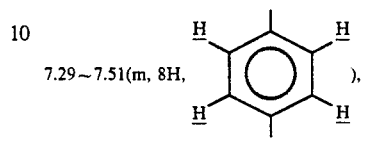),

EXAMPLE 37

The same procedure as in Example 1 was repeated except that 6.2 parts of ethylene glycol was replaced with 19.6 parts of tricyclo[5,2,1,0$^{2,6}$]decane-4,8-dimethanol, thereby obtaining 55.9 parts of 4,8-bis[N-(3-isopropenyl-α,α-dimethylbezyl)carbamoyloxymethyl]tricyclo [5,2,1,0$^{2.6}$]decane in the form of a colorless transparent liquid.

| Values of elemental analysis (as $C_{38}H_{50}N_2O_4$) | | | |
|---|---|---|---|
| | C | H | N |
| Found (%) | 76.27 | 8.69 | 4.55 |
| Calcd. (%) | 76.22 | 8.42 | 4.68 |

NMR(δ/CDCl₃)

δ=0.70~2.50(m, 34H, 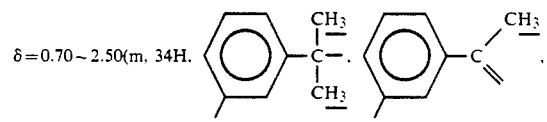.

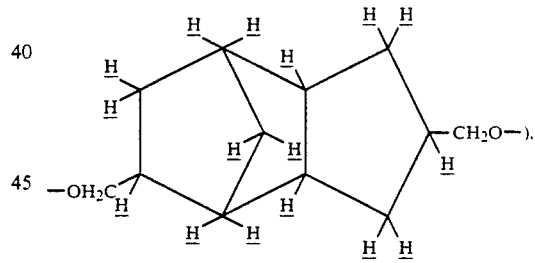

3.73(s, 4H, 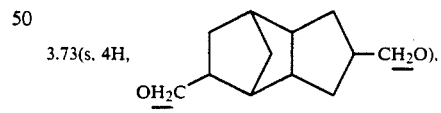), 5.07(s, 4H, 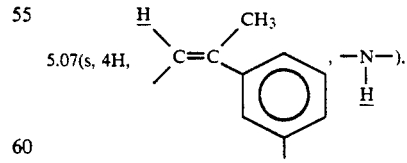, —N—).

5.34(s, 2H, 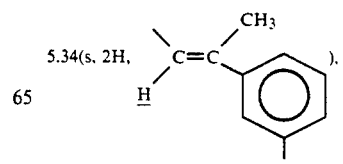), 7.30(s, 6H, 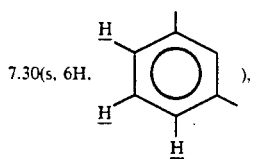), 7.48(s, 2H, 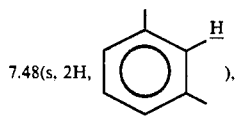),

EXAMPLE 38

The same procedure as in Example 2 was repeated except that 6.2 parts of ethylene glycol was replaced with 19.6 parts of tricyclo[5,2,1,0$^{2,6}$]decane-4,8-dimethanol, thereby obtaining 54.8 parts of 4,8-bis[N-(4-isopropenyl-α,α-dimethylbenzyl)carbamoylmethyl]tricyclo[5,2,1,0$^{2,6}$decane in the form of a colorless transparent liquid.

| Values of elemental analysis (as C$_{38}$H$_{50}$N$_2$O$_4$) | | | |
|---|---|---|---|
| | C | H | N |
| Found (%) | 76.19 | 8.65 | 4.32 |
| Calcd. (%) | 76.22 | 8.42 | 4.68 |

NMR(δ/CDCl$_3$)

δ = 0.70~2.50(m, 34H,
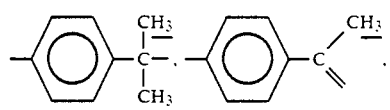

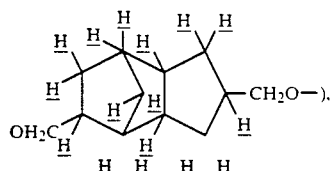

3.73(s, 4H, 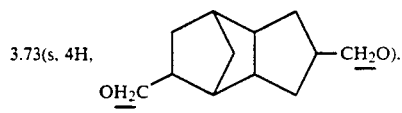

5.08(s, 4H, 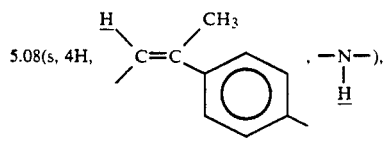

5.39(s, 2H, 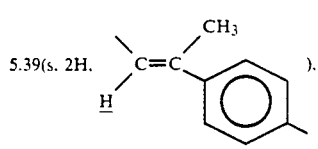

7.36(s, 8H, 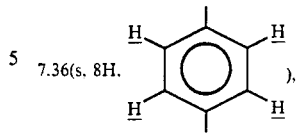

EXAMPLE 39

The same procedure as in Example 1 was repeated except that 6.2 parts of ethylene glycol was replaced with 11.1 parts of 3-chloro-1,2-propanediol, thereby obtaining 49.2 parts of 3-chloro-1,2-bis[N-(3-isopropenyl-α,α-dimethylbenzyl)carbamoyloxy]propane in the form of a colorless transparent liquid.

| Values of elemental analysis (as C$_{29}$H$_{37}$N$_2$O$_4$Cl) | | | | |
|---|---|---|---|---|
| | C | H | N | Cl |
| Found (%) | 67.72 | 7.31 | 5.35 | 6.98 |
| Calcd. (%) | 67.89 | 7.27 | 5.46 | 6.91 |

NMR(δ/CDCl$_3$)

δ = 1.66(s, 12H, 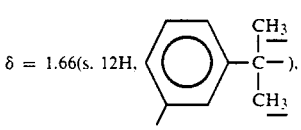), 2.14(s, 6H, 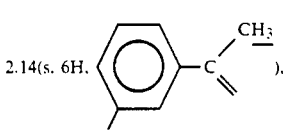), 3.60(s, 2H, —OCH$_2$CHO—), 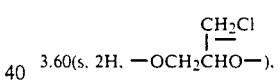

4.13(s, 2H, —OCH$_2$CHO—), 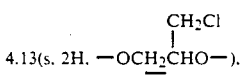

4.90~5.40(m, 7H, —OCH$_2$CHO—, 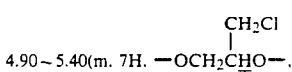

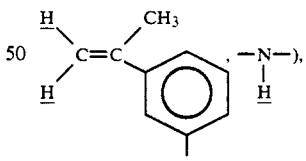

7.29(s, 6H, 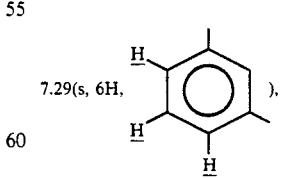), 7.47(s, 2H, 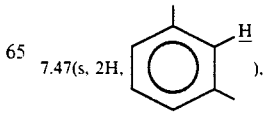),

EXAMPLE 40

The same procedure as in Example 2 was repeated except that 6.2 parts of ethylene glycol was replaced with 11.1 parts of 3-chloro-1,2-propanediol, thereby obtaining 49.8 parts of 3-chloro-1,2-bis[N-(4-isopropenyl-α,α-dimethylbenzyl)carbamoyloxy]propane in the form of a colorless transparent liquid.

| Values of elemental analysis (as $C_{29}H_{37}N_2O_4Cl$) | | | | |
|---|---|---|---|---|
| | C | H | N | Cl |
| Found (%) | 68.04 | 7.31 | 5.24 | 6.83 |
| Calcd. (%) | 67.89 | 7.27 | 5.46 | 6.91 |

NMR(δ/CDCl$_3$)

δ = 1.66(s, 12H, 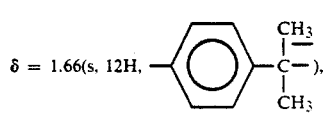

2.14(s, 6H, 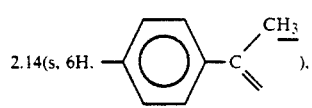

3.60(s, 2H, 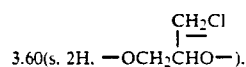

4.13(s, 2H, 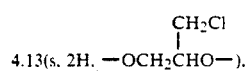

4.90~5.43(m, 7H, 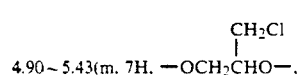

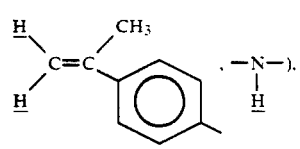, —N—), 7.35(s, 8H, 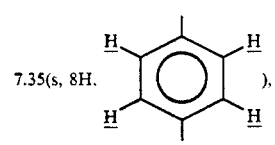

EXAMPLE 41

The same procedure as in Example 1 was repeated except that 6.2 parts of ethylene glycol was replaced with 15.5 parts of 3-bromo-1,2-propanediol, thereby obtaining 51.4 parts of 3-bromo-1,2-bis[N-(4-isopropenyl-α,α-dimethylbenzyl)carbamoyloxy]propane in the form of a colorless transparent liquid.

| Values of elemental analysis (as $C_{29}H_{37}N_2O_4Br$) | | | | |
|---|---|---|---|---|
| | C | H | N | Br |
| Found (%) | 62.31 | 6.49 | 5.21 | 14.08 |
| Calcd. (%) | 62.48 | 6.69 | 5.02 | 14.33 |

NMR(δ/CDCl$_3$)

δ = 1.66(s, 12H, 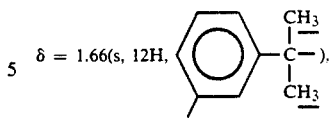

2.14(s, 6H, 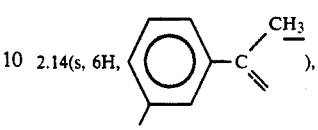

3.49(s, 2H, —OCH$_2$CHO—),
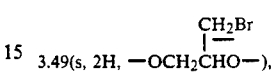

4.13(s, 2H, —OCH$_2$CHO—),
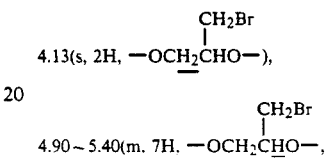

4.90~5.40(m, 7H, —OCH$_2$CHO—,
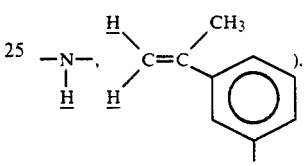

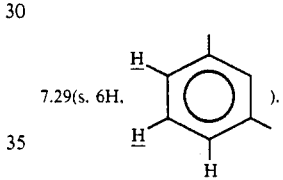

7.29(s, 6H, 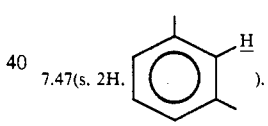

7.47(s, 2H, ).

EXAMPLE 42

The same procedure as in Example 2 was replaced except that 6.2 parts of ethylene glycol was replaced with 15.5 parts of 3-bromo-1,2-propanediol, thereby obtaining 52.3 parts of 3-bromo-1,2-bis[N-(4-isopropenyl-α,α-dimethylbenzyl)carbamoyloxy]propane in the form of a colorless transparent liquid.

| Values of elemental analysis (as $C_{29}H_{37}N_2O_4Br$) | | | | |
|---|---|---|---|---|
| | C | H | N | Br |
| Found (%) | 62.29 | 6.81 | 5.13 | 14.15 |
| Calcd. (%) | 62.48 | 6.69 | 5.02 | 14.33 |

NMR(δ/CDCl$_3$)

δ = 1.66(s, 12H, 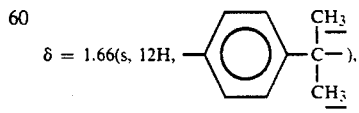

2.14(s, 6H, 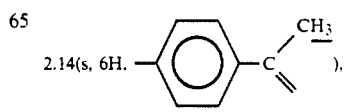

3.49(s, 2H, —OCH₂CHO—), 4.13(s, 2H, —OCH₂CHO—), 4.90~5.43(m, 7H, —OCH₂CHO—,

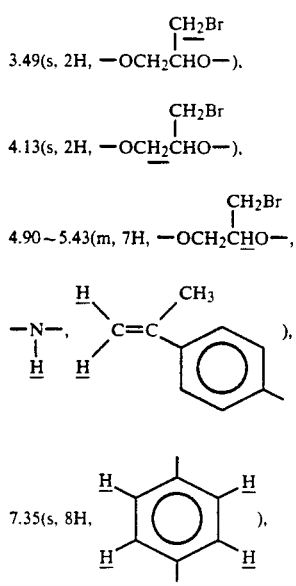

7.35(s, 8H, )

EXAMPLE 43

The same procedure as in Example 1 was repeated except that 6.2 parts of ethylene glycol was replaced with 24.8 parts of 2,3-dibromo-1,4-butanediol, thereby obtaining 59.8 parts of 2,3-dibromo-1,4-bis[N-(3-isopropenyl-α,α-dimethylbenzyl)carbamoyloxy]butane in the form of a colorless transparent liquid.

| Values of elemental analysis (as C₃₀H₃₈N₂O₄Br₂) | | | | |
|---|---|---|---|---|
| | C | H | N | Br |
| Found (%) | 55.58 | 5.93 | 4.25 | 24.79 |
| Calcd. (%) | 55.40 | 5.89 | 4.31 | 24.57 |

NMR(δ/CDCl₃)

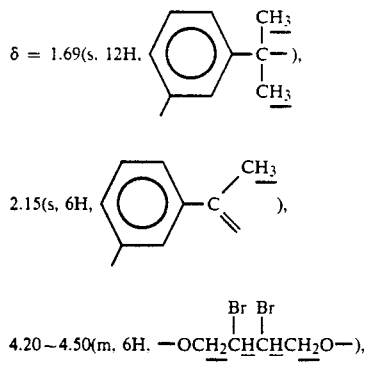

4.20~4.50(m, 6H, —OCH₂CHCHCH₂O—),

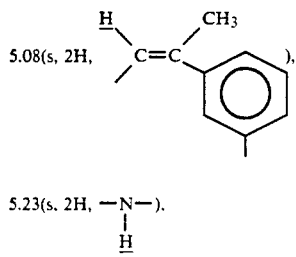

5.23(s, 2H, —N—),
            |
            H

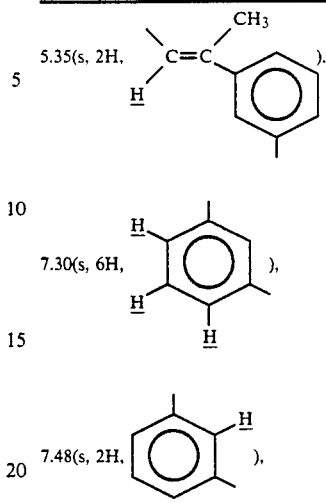

7.30(s, 6H, )

7.48(s, 2H, )

EXAMPLE 44

The same procedure as in Example 2 was repeated except that 6.2 parts of ethylene glycol was replaced with 24.8 parts of 2,3-dibromo-1,4-butanediol, thereby obtaining 57.6 parts of 2,3-dibromo-1,4-bis[N-(4-isopropenyl-α,α-dimethylbenzyl)carbamoyloxy]butane in the form of a colorless transparent liquid.

| Values of elemental analysis (as C₃₀H₃₈N₂O₄Br₂) | | | | |
|---|---|---|---|---|
| | C | H | N | Br |
| Found (%) | 55.28 | 5.69 | 4.53 | 24.72 |
| Calcd. (%) | 55.40 | 5.89 | 4.31 | 24.57 |

NMR(δ/CDCl₃)

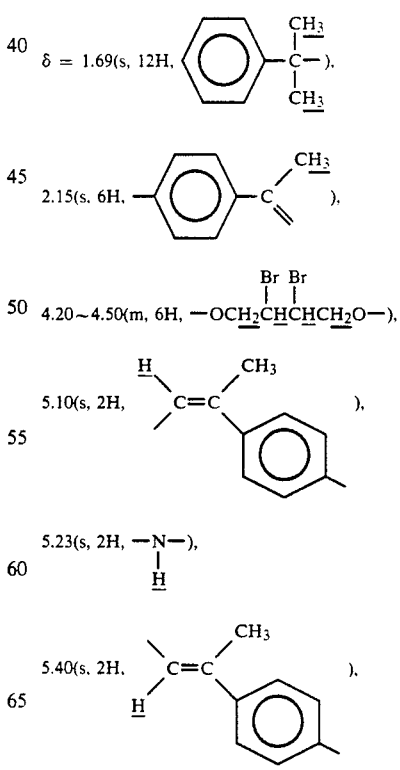

4.20~4.50(m, 6H, —OCH₂CHCHCH₂O—), 5.23(s, 2H, —N—),
            |
            H 7.36(s. 8H, 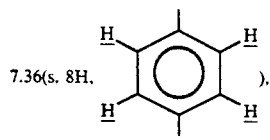).

EXAMPLE 45

The same procedure as in Example 1 was repeated except that 6.2 parts of ethylene glycol was replaced with 26.2 parts of dibromoneopentyl glycol, thereby obtaining 62.1 parts of 2,2-dibromomethyl-1,3-[N-(3-isopropenyl-α,α-dimethylbenzyl)carbamoyloxy]propane in the form of a colorless transparent liquid.

| Values of elemental analysis (as $C_{31}H_{40}N_2O_4Br_2$) | | | | |
|---|---|---|---|---|
| | C | H | N | Br |
| Found (%) | 55.93 | 6.14 | 4.18 | 24.00 |
| Calcd. (%) | 56.04 | 6.07 | 4.22 | 24.05 |

NMR(δ/CDCl₃)

δ = 1.63(s, 12H, 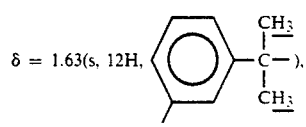), 2.15(s, 6H. 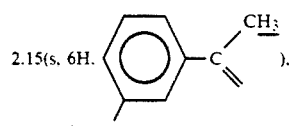), 3.40~4.20(m, 4H, 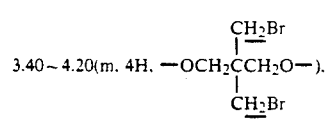), 5.10(s, 2H, 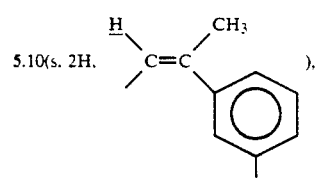), 5.40(s, 4H, 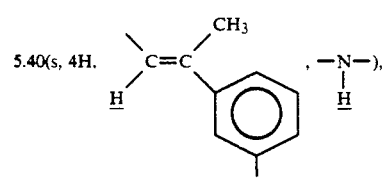), 7.34(s, 6H, 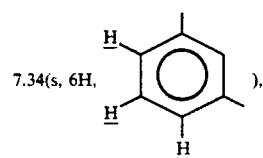), 7.55(s, 2H, 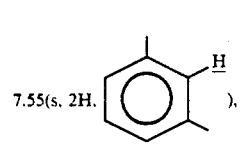),

EXAMPLE 46

The same procedure as in Example 2 was repeated except that 6.2 parts of ethylene glycol was replaced with 26.2 parts of dibromoneopentyl glycol, thereby obtaining 63.2 parts of 2,2-dibromomethyl-1,3-bis[N-(4-isopropenyl-α,α-dimethylbenzyl)carbamoyloxy]propane in the form of a colorless transparent liquid.

| Values of elemental analysis (as $C_{31}H_{40}N_2O_4Br_2$) | | | | |
|---|---|---|---|---|
| | C | H | N | Br |
| Found (%) | 56.21 | 6.03 | 4.39 | 24.32 |
| Calcd. (%) | 56.04 | 6.07 | 4.22 | 24.05 |

NMR(δ/CDCl₃)

δ = 1.63(s, 12H, 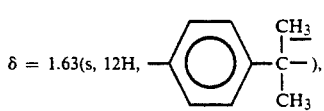), 2.15(s, 6H. 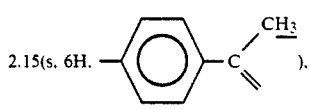), 3.40~4.20(m. 4H, 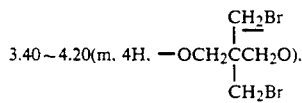), 5.11(s. 2H. 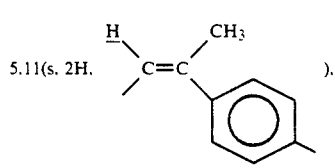), 5.42(s, 4H, 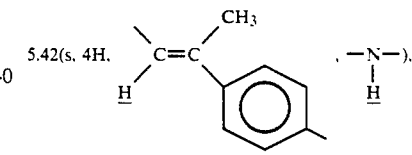, —N—), 7.41(s, 8H, 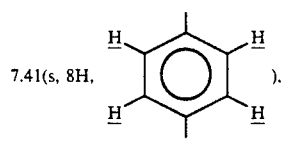),

EXAMPLE 47

6.1 parts of glycerol, 30 parts of toluene, 40.3 parts of 3-isopropenyl-α,α-dimethylbenzyl isocyanate and 0.2 part of dibutyltin dilaurate were mixed. The solution was then stirred for 1 hour, while the temperature of the solution was maintained at 90° C., to carry out the reaction. After completion of the reaction, the reaction solution was concentrated. The resulting concentrate was then purified by chromatography, thereby obtaining 42.4 parts of 1,2,3-tris[N-(3-isopropenyl-αα-dimethylbenzyl)carbamoyloxy]propane.

| Values of elemental analysis (as $C_{42}H_{53}N_3O_6$) | | | |
|---|---|---|---|
| | C | H | N |
| Found (%) | 72.26 | 7.71 | 6.09 |
| Calcd. (%) | 72.49 | 7.68 | 6.04 |

NMR(δ/CDCl₃)

δ = 1.63(s, 18H, 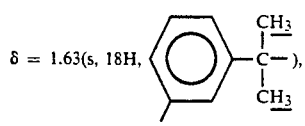

2.14(s, 9H, 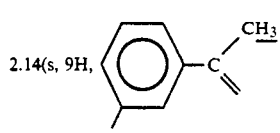

4.09(d, 4H, —OC<u>H</u>₂CHC<u>H</u>₂O—)

4.79~5.20(m, 7H, 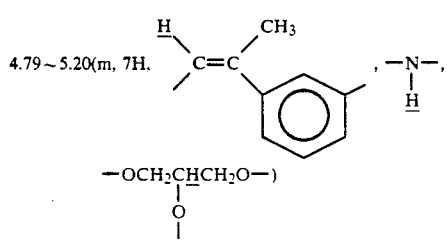

—OCH₂C<u>H</u>CH₂O—)

5.34(s, 3H, 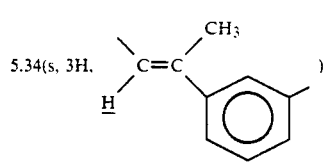

7.28(s, 9H, 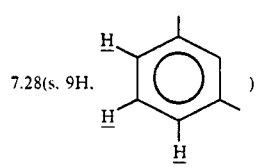

7.47(s, 3H, 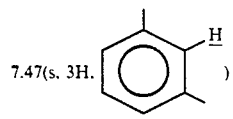

EXAMPLE 48

6.1 parts of glycerol, 30 parts of toluene, 26.8 parts of 3-isopropenyl-α,α-dimethylbenzyl isocyanate and 0.2 part of dibutyltin dilaurate were mixed. The solution was then stirred for 1 hour, while the temperature of the solution was maintained at 60° C. Afterward, 13.4 parts of 4-isopropenyl-α,α-dimethylbenzyl isocyanate was added thereto, and the solution was stirred for 1 hour, maintaining the temperature of the solution at 80° C., to carry out reaction. After completion of the reaction, the reaction solution was concentrated. The resulting concentrate was then purified by chromatography, thereby obtaining 41.3 parts of 1,3-bis[N-(3-isopropenyl- , -dimethylbenzyl) carbamoyloxy]-2-[N-4-isopropenyl- , -dimethylbenzyl)carbamoyloxy]propane in the form of a colorless transparent liquid.

Values of elemental analysis (as C₄₂H₅₃N₃O₆)

| | C | H | N |
|---|---|---|---|
| Found (%) | 72.31 | 7.74 | 6.17 |
| Calcd. (%) | 72.49 | 7.68 | 6.04 |

NMR(δ/CDCl₃)

δ = 1.64(s, 18H, 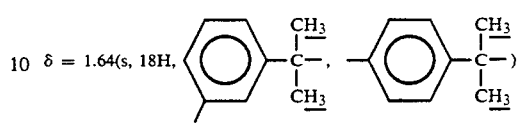

2.13(s, 9H, 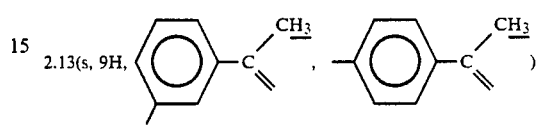

4.09(d, 4H, —OC<u>H</u>₂CHC<u>H</u>₂O—)

4.79~5.23(m, 7H, 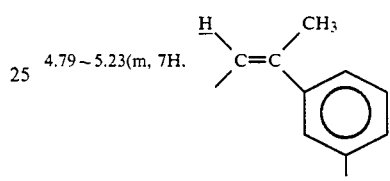

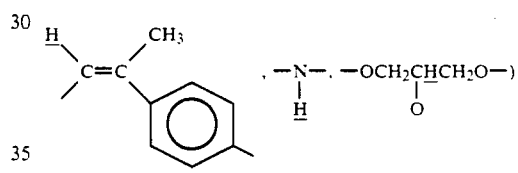

5.35(s, 3H, 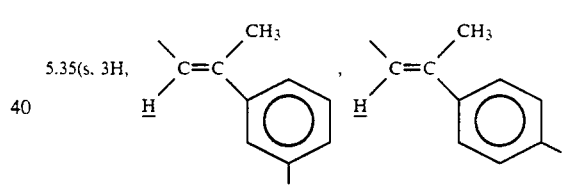

7.26~7.50(m, 12H, 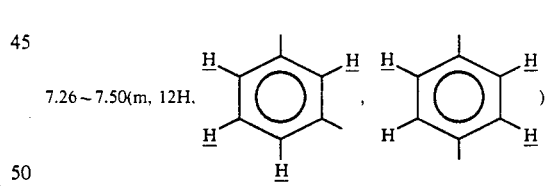

EXAMPLE 49

The same procedure as in Example 47 was repeated except that 6.1 parts of ethylene glycol was replaced with 8.0 parts of trimethylolethane, thereby obtaining 44.5 parts of 1,1,1-tris[N-(3-isopropenyl-α,α-dimethylbenzyl)carbamoyloxymethyl]ethane in the form of a colorless transparent liquid.

Values of elemental analysis (as C₄₄H₅₇N₃O₆)

| | C | H | N |
|---|---|---|---|
| Found (%) | 72.87 | 7.98 | 5.75 |
| Calcd. (%) | 73.00 | 7.94 | 5.80 |

NMR(δ/CDCl₃)

δ = 0.92(s, 3H, —OCH₂CCH₂O—) 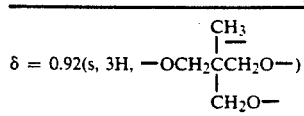

1.65(s, 18H, 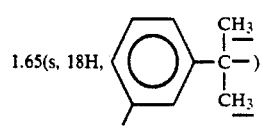)

2.14(s, 9H, 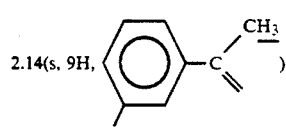)

3.89(s, 6H, —OH₂CCH₂O—) 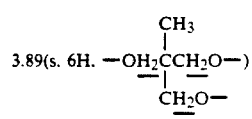

5.06(s, 6H, 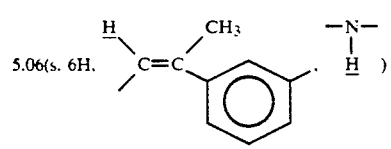)

5.33(s, 3H, 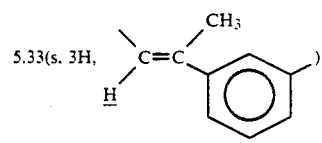)

7.28(s, 9H, 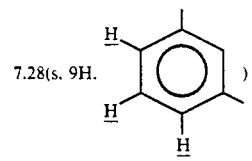)

7.47(s, 3H, 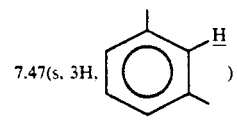)

EXAMPLE 50

The same procedure as in Example 47 was repeated except that 6.1 parts of glycerol was replaced with 8.9 parts of trimethylolpropane, thereby obtaining 42.7 parts of 2-ethyl-2-[N-(3-isopropenyl)-α,α-dimethylbenzyl)carbamoyloxymethyl]-1,3-[N-(3-isopropenyl-α,α-dimethylbenzyl)carbamoyloxy]propane in the form of a colorless transparent liquid.

| Values of elemental analysis (as C₄₅H₅₉N₃O₆) | | | |
|---|---|---|---|
| | C | H | N |
| Found (%) | 73.06 | 8.14 | 5.65 |
| Calcd. (%) | 73.24 | 8.06 | 5.69 |

NMR(δ/CDCl₃)

δ = 0.60~1.78(m, 23H, —OCH₂CCH₂O—, 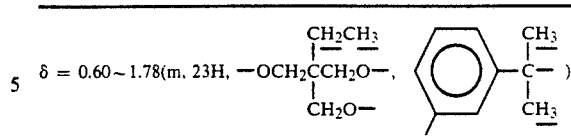)
  |
  CH₂O—

2.13(s, 9H, 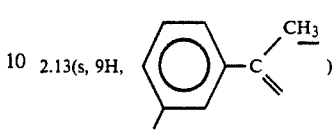)

3.91(s, 6H, —OCH₂CCH₂O—) 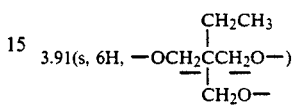

5.07(s, 6H, 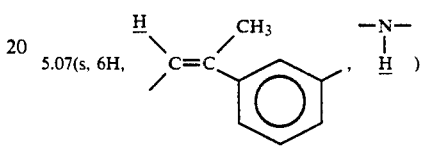)

5.33(s, 3H, 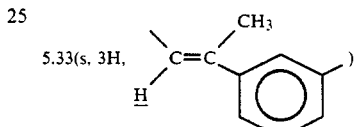)

7.28(s, 9H, 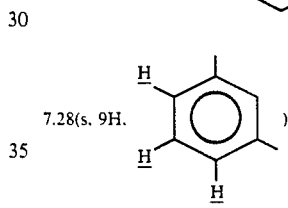)

7.46(s, 3H, 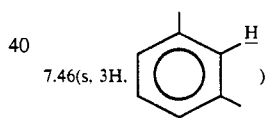)

EXAMPLE 51

8.9 parts of trimethylolpropane, 30 parts of toluene, 13.4 parts of 3-isopropenyl-α,α-dimethylbenzyl isocyanate, 26.8 parts of 4-isopropenyl-α,α-dimethylbenzyl isocyanate and 0.2 part of dibutyltin dilaurate were mixed. The solution was then stirred for 1 hour, while the temperature of the solution was maintained at 80° C., to carry out the reaction. After completion of the reaction, the reaction solution was concentrated. The resulting concentrate was then purified by chromatography, thereby obtaining 43.5 parts of 2-ethyl-2-[N-(3-isopropenyl-α,α-dimethylbenzyl)carbamoyloxymethyl]-1,3-[N-(4-isopropenyl-α,α-dimethylbenzyl)carbamoyloxy] propane in the form of a colorless transparent liquid.

| Values of elemental analysis (as C₄₅H₅₉N₃O₆) | | | |
|---|---|---|---|
| | C | H | N |
| Found (%) | 73.17 | 8.04 | 5.73 |
| Calcd. (%) | 73.24 | 8.06 | 5.69 |

NMR(δ/CDCl₃)

δ = 0.60~1.80(m, 23H, 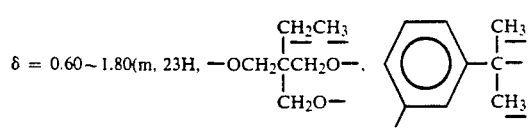

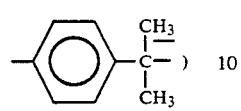

2.12(s, 9H, 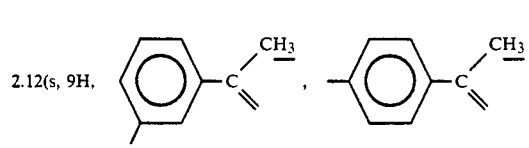

3.91(s, 6H, 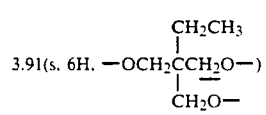

5.08(s, 6H, 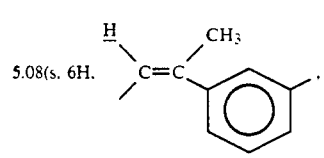

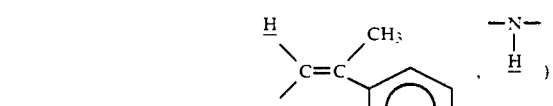

5.34(s, 3H, 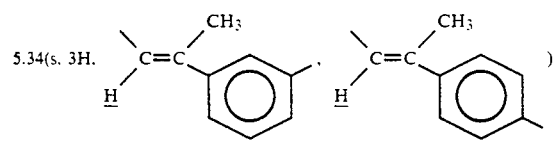

7.26~7.50(m, 12H, 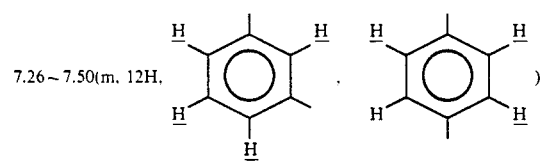

EXAMPLE 52

The same procedure as in Example 47 was repeated except that 6.1 parts of glycerol was replaced with 7.1 parts of 1,2,4-butanetriol, thereby obtaining 41.8 parts of 1,2,4-tris]N-(3-isopropenyl-α,α-dimethylbenzyl)carbamoyloxy]butane in the form of a colorless transparent liquid.

| Values of elemental analysis (as C₄₃H₅₅N₃O₆) | | | |
|---|---|---|---|
| | C | H | N |
| Found (%) | 72.81 | 7.79 | 5.96 |
| Calcd. (%) | 72.75 | 7.81 | 5.92 |

NMR(δ/CDCl₃)

δ = 1.48~1.96(m, 20H, 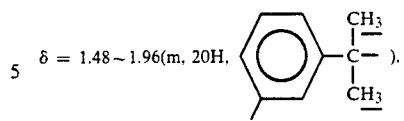

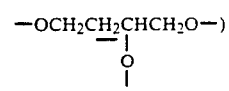

2.13(s, 9H, 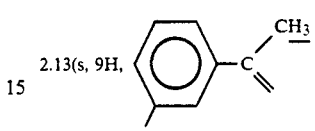

4.04(d, 4H, 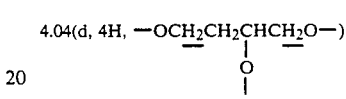

4.86~5.28(m, 7H, 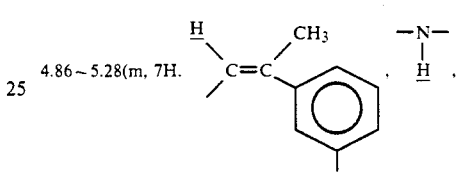

5.34(s, 3H, 

7.28(s, 9H, 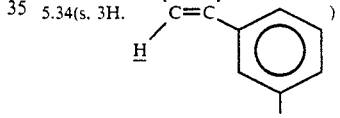

7.46(s, 3H, 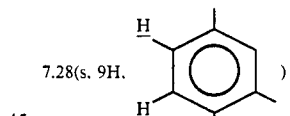

EXAMPLE 53

The same procedure as in Example 47 was repeated except that 6.1 parts of glycerol was replaced with 17.4 parts of 1,3,5-tris(2-hydroxyethyl)cyanuric acid. The reaction solution was maintained under toluene reflux, thereby obtaining 49.9 parts of 1,3,5-tris[2-(N-(3-isopropenyl-, -dimethylbenzyl)-carbamoyloxethyl)] isocyanurate in the form of a colorless transparent liquid.

| Values of elemental analysis (as C₄₈H₆₀N₆O₉) | | | |
|---|---|---|---|
| | C | H | N |
| Found (%) | 66.73 | 6.87 | 9.81 |
| Calcd. (%) | 66.65 | 6.99 | 9.72 |

NMR(δ/CDCl₃)

δ = 1.58(s, 18H, 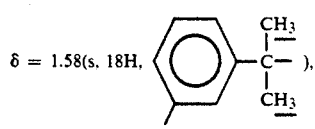), 2.13(s, 9H, 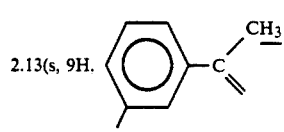), 4.10(s, 6H, 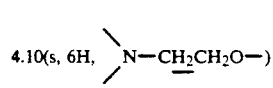), 4.25(s, 6H, 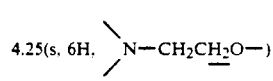), 5.06(s, 3H, 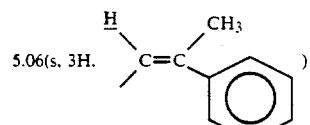), 5.34(s, 3H, 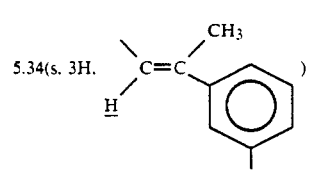), 5.41(s, 3H, 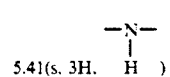), 7.26(s, 9H, 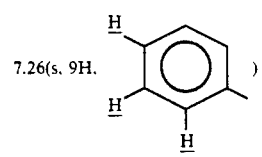), 7.45(s, 3H, 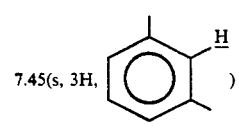)

EXAMPLE 54

17.4 parts of 1,3,4-tris(2-hydroxyethyl)cyanuric acid, 30 parts of toluene, 26.8 parts of 3-isopropenyl-α,α-methylbenzyl isocyanate, 13.4 parts of 4-isopropenyl-α,α-dimethylbenzyl isocyanate and 0.2 part of dibutyltin dilaurate were mixed. The solution was then stirred for 1 hour under reflux, to carry out reaction. After completion of the reaction, the reaction solution was concentrated. The resulting concentrate was then purified by chromatography, thereby obtaining 51.4 parts of 1,3-bis[2-[N-(3-isopropenyl-α,α-dimethylbenzyl)carbamoyloxyethyl]]] isocyanurate in the form of a colorless transparent liquid.

| Values of elemental analysis (as $C_{48}H_{60}N_6O_9$) | | | |
|---|---|---|---|
| | C | H | N |
| Found (%) | 66.58 | 7.05 | 9.63 |
| Calcd. (%) | 66.65 | 6.99 | 9.72 |

NMR(δ/CDCl₃)

δ = 1.59(s, 18H, 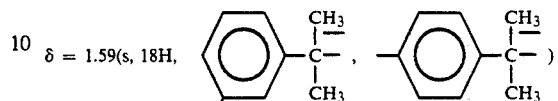)

2.14(s, 9H, 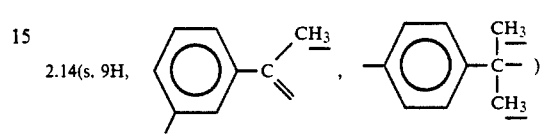)

4.10(s, 6H, 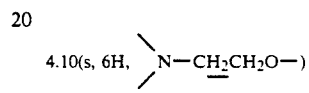)

4.25(s, 6H, 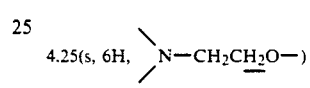)

5.07(s, 3H, 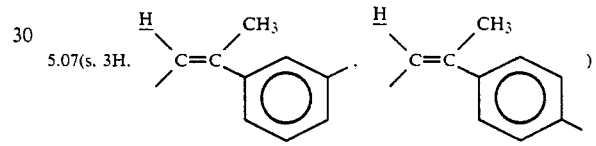)

5.30~5.43(m, 6H, 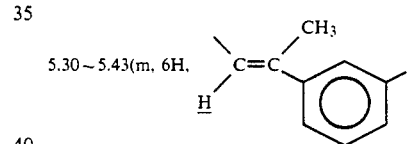)

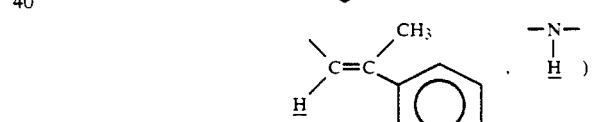

7.25~7.48(m, 12H, 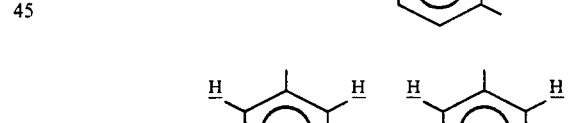)

In the following examples, the high surface hardness transparent resin of the present invention will be described in detail.

EXAMPLE 55

201 parts of 3-isopropenyl-α,α-dimethylbenzylisocyanate was mixed with 1 part of dibutyltin dilaurate and 100 parts of methanol, and the mixture was then stirred for 30 minutes under methanol reflux in order to carry out the reaction. After completion of the reaction, methanol was distilled off, and the residue was then purified through a chromatography, thereby obtaining 198 parts of a colorless liquid monomer having the following structure:

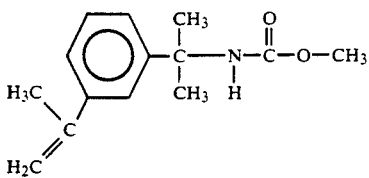

To 116.7 parts of the monomer thus prepared added 70.6 parts of tris(acryloyloxyethyl) isocyanurate, and they were then mixed sufficiently. Afterward, 1.9 parts of benzoyl peroxide was added thereto, followed by mixing and defoaming. This solution was then poured into a mold prepared by interposing a 5-mm-thick polyvinyl chloride spacer between peripheral portions of two 5-mm-thick glass plates and then firmly fastening them together with a clamp, and polymerization was effected in a hot-air oven for polymerization by elevating the temperature therein rom 70° C. to 150° C. over 1.5 hours. After cooling, a transparent resin plate having a smooth surface was released from the mold.

EXAMPLE 56

17.6 parts of pentaerythritol tetraacrylate and 0.3 part of benzoyl peroxide were added to 23.2 parts of 1,2-bis[N-(3-isopropenyl-$\alpha,\alpha$,-dimethylbenzyl)carbamoyloxy]ethane obtained by the same procedure as in Example 1, followed by sufficient mixing and defoaming. The resulting uniformed solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

EXAMPLE 57

17.6 parts of pentaerythritol tetraacrylate and 0.3 part of benzoyl peroxide were added to 23.2 parts of 1,2-bis[N-(4-isopropenyl-$\alpha,\alpha$-dimethylbenzyl)carbamoyloxy]-ethane obtained by the same procedure as in Example 2, followed by sufficient mixing and defoaming. The resulting uniformed solution was then poured into a mold prepared by interposing a 5-mm-thick polyvinyl chloride spacer between peripheral portions of two 5-mm-thick glass plates, and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

EXAMPLE 58

33.4 parts of trimethylolpropane trimethacrylate and 0.3 part of benzoyl peroxide were added to 25.4 parts of bis[2-(N-(3-isopropenyl-$\alpha,\alpha$-dimethylbenzyl)carbamoyloxy)-ethyl] ether obtained by the same procedure as in Example 19, followed by sufficient mixing and defoaming. The resulting solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

EXAMPLE 59

20.0 parts of ethyl acrylate and 0.3 part of benzoyl peroxide were added to 29.9 parts of 4,8-bis[N-(3-isopropenyl-$\alpha,\alpha$-dimethylbenzyl)carbamoyloxymethyl]-tricyclo[5,2,-1,0$^{2,6}$]decane obtained by the same procedure as in Example 37, followed by sufficient mixing and defoaming. The resulting uniformed solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

EXAMPLE 60

26.4 parts of pentaerythritol tetraacrylate and 0.3 part of benzoyl peroxide were added to 31.7 parts of 1,2,3-tris[N-(3-isopropenyl-$\alpha,\alpha$-dimethylbenzyl)carbamoyloxy]propane obtained by the same procedure as in Example 47, followed by sufficient mixing and defoaming. The resulting uniformed solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

EXAMPLE 61

42.3 parts of tris(acryloyloxyethyl)isocyanurate and 0.4 part of benzoyl peroxide were added to 43.3 parts of 1,3,5-tris[2-(N-(3-isopropenyl-$\alpha,\alpha$-dimethylbenzyl)carbamoyloxyethyl]isocyanurate obtained by the same procedure as in Example 53, followed by sufficient mixing and defoaming. The resulting solution was then poured into a mold prepared by interposing a 5-mm-thick polyvinyl chloride spacer between peripheral portions of two 5-mm-thick glass plates and then firmly fastening them together with a clamp.

Polymerization was then effected in a hot-air oven for polymerization by elevating the temperature therein from 70° C. to 150° C. over 1.5 hours. After cooling, a transparent resin plate having a smooth surface was released from the mold.

EXAMPLE 62

11.5 parts of glycerol and 0.5 part of dibutyltin dilaurate were added to 100.6 parts of 3-isopropenyl-$\alpha,\alpha$-dimethylbenzyl isocyanate, and the mixture was then heated with stirring for 1 hour so that an internal temperature might be 80° C. After cooling, 4.0 parts of methanol was added thereto, and heating was then carried out with stirring for 1 hour so that the internal temperature might be 55° C., in order to obtain a mixture of two kinds of urethane compounds. To this mixture, 92.0 parts of pentaerythritol tetraacrylate was added, followed by mixing and defoaming. This solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

denoted by "○", and the plates which could not be done were denoted by "X".

TABLE 1

| Test Item | Example 55 | Example 56 | Example 57 | Example 58 | Example 59 | Example 60 | Example 61 | Example 62 | Example 63 |
|---|---|---|---|---|---|---|---|---|---|
| Appearance | ○ | ○ | ○ | ○ | ○ | ○ | ○ | ○ | ○ |
| Surface Hardness | 5H | 9H or more | 9H or more | 4H | 4H | 9H or more | 6H | 9H or more | 9H or more |
| Heat Resistance | ○ | ○ | ○ | ○ | ○ | ○ | ○ | ○ | ○ |
| Chemical Resistance | ○ | ○ | ○ | ○ | ○ | ○ | ○ | ○ | ○ |
| Workability | ○ | ○ | ○ | ○ | ○ | ○ | ○ | ○ | ○ |

EXAMPLE 63

11.6 parts of ethylene glycol and 0.1 part of dibutyltin dilaurate were added to 75.5 parts of 3-isopropenyl-α,α-dimethylbenzyl isocyanate, and the mixture was then heated with stirring for 1 hour so that an intenal temperature might be 70° C. Afterward, 41.5 parts of N-(3-isopropenyl-α,α-dimethylbenzyl)-2-methacryloyloxy carbamate was added thereto.

88.1 parts of pentaerythritol tetraacrylate and 1.0 part of benzoyl peroxide were added thereto, followed by sufficient mixing and defoaming. The solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

For the transparent resin plates obtained in Examples 55 to 63, various physical properties were measured. The results are set forth in Table 1.

In measuring these physical properties, the following procedures were employed:

(1) Appearance: The appearance of each polymer plate was evaluated by observing the same by the naked eye. The polymer plates which were free from cracks and a rough surface were denoted by "○", and the plates having such disadvantages were denoted by "X".

(2) Surface Hardness This was measured by the use of a pencil scratching test machine for coating films under JIS-K-5401.

(3) Heat Resistance: The resin plates were allowed to stand at 120° C. for 4 hours in a hot-air drier Afterward, the resin plates were observed by the naked eye. The plates which were free from coloring and strain on the surfaces thereof were denoted by "○" and the plates having such drawbacks were denoted by "X".

(4) Chemical Resistance: The polymer plates were immersed in isopropanol and toluene at room temperature for 24 hours. Afterward, they were scratched with an HB pencil The plates which were free from any traces were denoted by "○", and the plates having some traces were denoted by "X".

(5) Workability: The plates which could be abraded by a lens polisher for spectacle lens processing were denoted by "○", and the plates which could not be done were denoted by "X".

EXAMPLE 64

0.1 part of benzoyl peroxide was added to 30 parts of a monomer mixture prepared by the same procedure as in Example 56, followed by sufficient mixing and defoaming. The mixture was then filtered through a filter having a pore diameter of 5 μm under pressure, and then poured into a +2 diopter lens mold for diethylene glycol diallyl carbonate. Afterward, polymerization was effected by elevating the temperature of the mixture from 70° C. to 140° C. over 3 hours. After cooling, a transparent convex lens having a smooth surface was released from the mold. The pencil hardness on the surface of the convex lens was 9H or more, and a refractive index by the Abbe's refractometer was 1.54.

EXAMPLE 65

0.2 part of benzoyl peroxide was added to 20.0 parts of a monomer mixture prepared by the same procedure as in Example 56 followed by mixing and defoaming.

The mixture was then applied onto a steel plate by the use of a coating bar so that a coating thickness might be 50 μm. Afterward, the mixture was cured at a temperature of 140° C. for 30 minutes, whereby a transparent coating film having a smooth surface was obtained on the steel plate. The pencil hardness of this coating film was 9H or more, and the results of a checker test (JIS K 5400) were good. In addition, heat resistance was also good (the specimens were allowed to stand at 120° C. for 10 hours in a hot-air drier, and those which were free from any problems were evaluated to be good).

COMPARATIVE EXAMPLE 1

3.0 parts of benzoyl peroxide was added to 100 parts of diethylene glycol diallyl carbonate, followed by mixing and defoaming. This solution was then poured into a mold prepared by interposing a 5-mm-thick polyvinyl chloride spacer between peripheral portions of two 5-mm-thick glass plates and then firmly fastening them together with a clamp, and it was tried that polymerization was effected in a hot-air oven for polymerization by elevating the temperature therein from 70° C. to 120° C. over 3 hours. However, when the temperature reached about 70° C. in the course of the polymerization, the polymerization advanced vigorously, so that the polymer was peeled from the glass mold and was colored yellow.

Only when the polymerization was carried out by elevating the temperature from 50° C. to 120° C. over 10 hours, a resin plate could be obtained without peeling from the mold, but the pencil hardness of the obtained resin was 3 H.

COMPARATIVE EXAMPLE 2

18.8 parts of m-xylylene diisocyanate was added to 20.0 parts of methyl methacrylate, and 0.5 part of dibutyltin laurate was further added thereto. 26.0 parts of hydroxyethyl methacrylate was slowly added thereto, while heating was carried out so that an internal temperature might be 60 °C., thereby obtaining a viscous methyl methacrylate mixture of an urethane compound in which the infrared spectrum absorption based on an isocyanate group was scarcely seen. 0.3 part of benzoyl peroxide was further added thereto, followed mixing and defoaming, and the solution was then poured into a mold prepared by interposing a 5-mm-thick polyvinyl chloride spacer between peripheral portions of two 5-mm-thick glass plates and then firmly fastening them together with a clamp, and it was tried that polymerization was effected in a hot-air oven for polymerization by elevating the temperature therein from 45° C. to 120° C. over 3 hours. However, when the temperature reached about 65° C. in the course of the polymerization, the polymerization advanced vigorously, so that the polymer was peeled from the glass mold.

COMPARATIVE EXAMPLE 3

0.5 part of benzoyl peroxide was added to 50 parts of trimethylolpropane triacrylate, followed mixing and defoaming. This solution was then poured into a mold prepared by interposing a 5-mm-thick polyvinyl chloride spacer between peripheral portions of two 5-mm-thick glass plates and then firmly fastening them together with a clamp, and it was tried that polymerization was effected in a hot-air oven for polymerization by elevating the temperature therein from 60° C. to 140° C. over 3 hours. However, at an early stage in the course of the polymerization, the polymerization advanced vigorously, so that the polymer was peeled from the glass mold.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A polymerizable monomer capable of forming a high surface hardness transparent resin by copolymerization with a monomer having a group selected from the group consisting of acryloyloxy group, methacryloyloxy group and vinylphenyl group and being represented by the formula (VII)

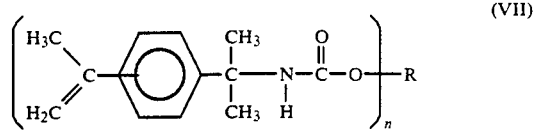

wherein n is 2 or 3, R is selected from the groups consisting of

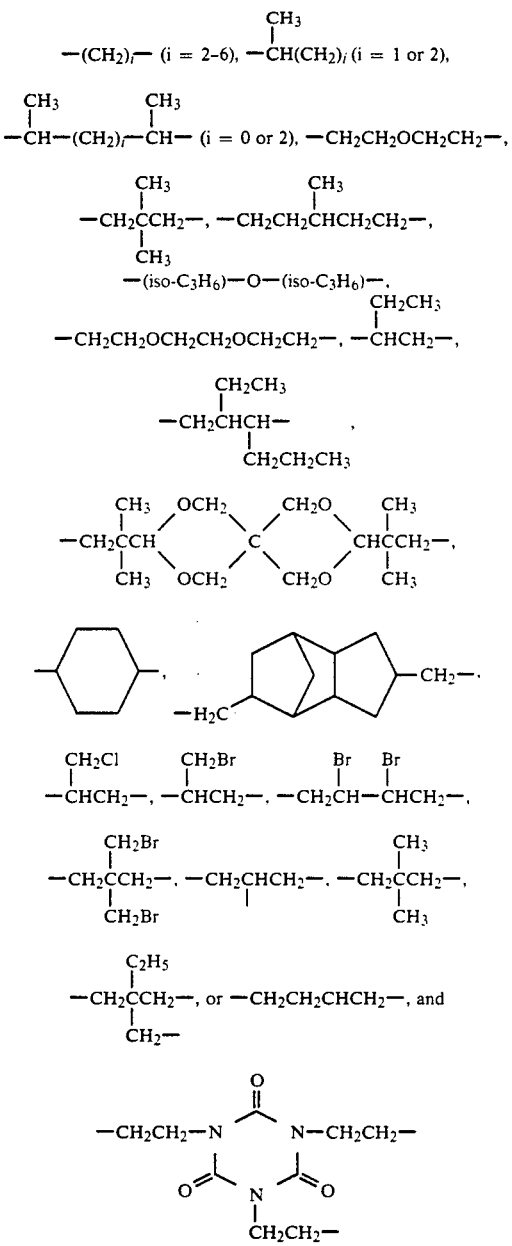

and the substituent on the aromatic ring is present at the m-position or the p-position thereof.

* * * * *

UNITED STATES PATENT AND TRADEMARK OFFICE
CERTIFICATE OF CORRECTION

PATENT NO. : 5,260,439

DATED : November 9, 1993

INVENTOR(S) : Toshiyuki SUZUKI et al

It is certified that error appears in the above-identified patent and that said Letters Patent is hereby corrected as shown below:

Claim 1, column 76, line 45,

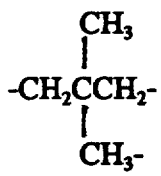

should be

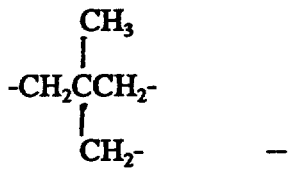

Claim 1, column 76, line 49, delete "or".

UNITED STATES PATENT AND TRADEMARK OFFICE
CERTIFICATE OF CORRECTION

PATENT NO.   : 5,260,439
DATED        : November 9, 1993
INVENTOR(S)  : Toshiyuki Suzuki et al It is certified that error appears in the above-indentified patent and that said Letters Patent is hereby corrected as shown below:

Claim 1, column 76, line 49, "-CH$_2$CH$_2$CHCH$_2$-" should be -- -CH$_2$CH$_2$CHCH$_2$- --.
$$\phantom{-CH_2CH_2C}|$$

Signed and Sealed this

Second Day of January, 1996

BRUCE LEHMAN

*Attest:*

*Attesting Officer*         Commissioner of Patents and Trademarks